(12) United States Patent
Matsui et al.

(10) Patent No.: US 11,666,133 B2
(45) Date of Patent: Jun. 6, 2023

(54) INFORMATION PROCESSING APPARATUS, PROGRAM, COSMETIC DISPENSER

(71) Applicant: SHISEIDO COMPANY, LTD., Tokyo (JP)

(72) Inventors: Yuko Matsui, Kanagawa (JP); Hideo Hata, Kanagawa (JP); Mayuri Tashiro, Kanagawa (JP); Mieko Nasu, Kanagawa (JP); Motoki Takata, Kanagawa (JP); Yohei Kobayashi, Kanagawa (JP); Miho Yajima, Kanagawa (JP); Youko Hayashi, Kanagawa (JP); Ayaka Nagai, Kanagawa (JP); Takanari Tsuda, Kanagawa (JP); Yuichiro Mori, Kanagawa (JP); Naoki Saito, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 580 days.

(21) Appl. No.: 16/635,255

(22) PCT Filed: Aug. 1, 2018

(86) PCT No.: PCT/JP2018/028797
§ 371 (c)(1),
(2) Date: Jan. 30, 2020

(87) PCT Pub. No.: WO2019/026942
PCT Pub. Date: Feb. 7, 2019

(65) Prior Publication Data
US 2021/0085060 A1    Mar. 25, 2021

(30) Foreign Application Priority Data

Aug. 4, 2017  (JP) .............................. JP2017-151692

(51) Int. Cl.
*A45D 44/00* (2006.01)
*G16H 40/67* (2018.01)
(Continued)

(52) U.S. Cl.
CPC ........... *A45D 44/005* (2013.01); *A45D 34/00* (2013.01); *A61B 5/4839* (2013.01);
(Continued)

(58) Field of Classification Search
CPC ............ A45D 44/005; A45D 2044/007; G07F 13/06; G06Q 30/0621; G16H 20/13
(Continued)

(56) References Cited

U.S. PATENT DOCUMENTS 9,138,041 B2 *  9/2015  Samain ................. G16H 20/13
9,498,974 B2   11/2016  Choi
(Continued)

FOREIGN PATENT DOCUMENTS

JP    2003-534621 A    11/2003
JP    2017-510389 A     4/2017
(Continued)

OTHER PUBLICATIONS

Extended European Search Report (EESR) dated Mar. 19, 2021 in European Application 18840956.9.
(Continued)

*Primary Examiner* — Timothy R Waggoner
(74) *Attorney, Agent, or Firm* — Morgan, Lewis & Bockius LLP

(57) ABSTRACT

Customized cosmetics corresponding to user-unique factors are provided.
An information processing apparatus can communicate with a cosmetic dispenser configured to dispense at least one of a plurality of cosmetics based on recipe information indicating a usage amount of each of the plurality of cosmetics.
(Continued)

The apparatus includes a retrieve module configured to retrieve user-unique information unique to the user, the user-unique information including at least one of user attribute information related to the user's attributes, environmental information related to the user's environment, action information related to the user's action, and psychosomatic information related to the user's psychosomatic, skin information related to the user's skin, and information related to cosmetics which the user has used, a selection module configured to select the recipe information based on the user unique information among a plurality of recipe information, and a transmission module configured to transmit the selected recipe information to the cosmetic dispenser.

18 Claims, 26 Drawing Sheets

(51) Int. Cl.
| | |
|---|---|
| *G16H 10/60* | (2018.01) |
| *G16H 50/30* | (2018.01) |
| *A45D 34/00* | (2006.01) |
| *A61B 5/00* | (2006.01) |
| *G06N 5/04* | (2023.01) |
| *G06Q 30/0201* | (2023.01) |
| *G16H 20/13* | (2018.01) |
| *B01F 33/84* | (2022.01) |
| *B01F 35/21* | (2022.01) |
| *A61B 5/024* | (2006.01) |
| *A61B 5/107* | (2006.01) |
| *A61B 5/16* | (2006.01) |
| *A61B 10/00* | (2006.01) |
| *G06Q 30/0202* | (2023.01) |
| *G06Q 30/0601* | (2023.01) |
| *H04L 67/12* | (2022.01) |
| *B01F 101/21* | (2022.01) |

(52) U.S. Cl.
CPC ........ *B01F 33/846* (2022.01); *B01F 33/8442* (2022.01); *B01F 35/2115* (2022.01); *B01F 35/2135* (2022.01); *G06N 5/04* (2013.01); *G06Q 30/0201* (2013.01); *G16H 10/60* (2018.01); *G16H 20/13* (2018.01); *G16H 40/67* (2018.01); *G16H 50/30* (2018.01); *A45D 2034/005* (2013.01); *A45D 2044/007* (2013.01); *A61B 5/024* (2013.01); *A61B 5/1072* (2013.01); *A61B 5/165* (2013.01); *A61B 5/442* (2013.01); *A61B 5/443* (2013.01); *A61B 5/444* (2013.01); *A61B 5/4806* (2013.01); *A61B 5/4866* (2013.01); *A61B 5/4872* (2013.01); *A61B 10/0012* (2013.01); *B01F 2101/21* (2022.01); *G06Q 30/0202* (2013.01); *G06Q 30/0631* (2013.01); *H04L 67/12* (2013.01)

(58) Field of Classification Search
USPC ........................................................ 700/236
See application file for complete search history.

(56) References Cited

U.S. PATENT DOCUMENTS

| | | | |
|---|---|---|---|
| 2003/0064356 A1* | 4/2003 | Rubinstenn | A61B 5/444 434/377 |
| 2005/0048461 A1* | 3/2005 | Lahteenmaki | G06Q 10/10 435/3 |
| 2014/0058755 A1* | 2/2014 | Macoviak | G06Q 10/10 705/2 |
| 2016/0015152 A1 | 1/2016 | Ajiki et al. | |
| 2016/0107133 A1 | 4/2016 | Sugino et al. | |
| 2016/0331308 A1* | 11/2016 | Zhou | A61M 35/003 |
| 2017/0154372 A1 | 6/2017 | Balooch et al. | |
| 2017/0208921 A1 | 7/2017 | Thiebaut et al. | |
| 2017/0360693 A1* | 12/2017 | Yakubov | A61Q 19/00 |
| 2018/0033205 A1* | 2/2018 | Kong | G06V 40/164 |
| 2018/0263551 A1* | 9/2018 | Kimura | A61B 5/0077 |
| 2020/0167552 A1* | 5/2020 | Taoka | A61B 5/1079 |

FOREIGN PATENT DOCUMENTS

| | | |
|---|---|---|
| WO | 01/91600 A2 | 12/2001 |
| WO | 2014-147940 A1 | 9/2014 |
| WO | 2015/004903 A1 | 1/2015 |
| WO | 2015/111002 A1 | 7/2015 |
| WO | 2016/087469 A1 | 6/2016 |
| WO | 2016/203461 A1 | 12/2016 |

OTHER PUBLICATIONS

International Search Report (with partial translation) and Written Opinion issued in corresponding International Patent Application No. PCT/JP2018/028797, dated Oct. 30, 2018.

* cited by examiner

FIG.5

| USER INFORMATION DATABASE | | | | | | | |
|---|---|---|---|---|---|---|---|
| USER ID | USER NAME | USER ATTRIBUTE | | | ESTIMATION FORMULA | USED COSMETIC ID | INQUIRY |
| | | GENDER | AGE | ADD | | | |
| U001 | U1 | FEMALE | 28 | TOKYO | f=a1*A+b1*B+c1*C+d1*D | PRO001 | · |
| U002 | U2 | MALE | 29 | CHIBA | f=a2*A+b2*B+c2*C+d2*D | PRO001 PRO002 | · |
| · | · | · | · | · | · | · | · |

*FIG.6*

| ENVIRONMENT LOG INFORMATION DATABASE (USER ID: U001) | | | | |
|---|---|---|---|---|
| ENVIORMENT LOG ID | DATE AND TIME | UV EXXPOSURE AMOUNT | TEMPERATURE | HUMIDITY |
| U001 | 2017/5/1 10:00 | 68 | 28 | 48 |
| U002 | 2017/5/1 11:00 | 72 | 32 | 46 |
| . | . | . | . | . |

FIG.7

| ACTION LOG INFORMATION DATABASE (USER ID: U001) | | | | | | |
|---|---|---|---|---|---|---|
| ACTION LOG ID | DATE AND TIME | ACTION | START TIME | END TIME | CALORIE CHANGE | LOCATION |
| ALOG001 | 2017/5/1 8:00 | MEAL | 7:30 | 8:00 | +200 | X1,Y1 |
| ALOG002 | 2017/5/1 9:00 | RUNNING | 8:30 | 9:00 | -500 | X2,Y2 |
| ALOG003 | 2017/5/1 12:00 | MEAL | 11:30 | 12:00 | +400 | X3,Y3 |
| ALOG004 | 2017/5/1 19:00 | MEAL | 18:00 | 19:00 | +1500 | X4,Y4 |
| ALOG005 | 2017/5/2 8:00 | SLEEPING | 22:00 | 8:00 | -1 | X1,Y1 |
| . | . | . | . | . | . | . |

FIG.8

| PSYCHOSOMATIC LOG INFORMATION DATABASE (USER ID: U001) | | | | | |
|---|---|---|---|---|---|
| PSYCHOSOMATIC LOG ID | DATE AND TIME | PULSE VALUE | ESTROUS CYCLE | STRESS | MINDFULNESS |
| BLOG001 | 2017/5/1 8:00 | 90 | 25 | S1 | M1 |
| BLOG002 | 2017/5/1 9:00 | 60 | 28 | S2 | M2 |
| . | . | . | . | . | . |

FIG.9

| SKIN LOG INFORMATION DATABASE (USER ID: U001) | | | | | |
|---|---|---|---|---|---|
| SKIN LOG ID | DATE AND TIME | SKIN IMAGE | SKIN COLOR | WATER CONTENT | SEBUM AMOUNT |
| SKL001 | 2017/5/1 8:00 | Sk1.jpg | 255,228,196 | WA1 | SE1 |
| SKL002 | 2017/5/1 22:00 | Sk2.jpg | 255,228,197 | WA2 | SE2 |
| SKL003 | 2017/5/2 7:45 | Sk3.jpg | 255,228,198 | WA3 | SE3 |
| SKL004 | 2017/5/2 22:15 | Sk4.jpg | 255,228,199 | WA4 | SE4 |
| · | · | · | · | · | · |

FIG.10

| SKIN EVALUATION LOG INFORMATION DATABASE (USER ID: U001) | | | |
|---|---|---|---|
| SKIN EVALUATOIN LOG ID | DATE AND TIME | SKIN SCORE | |
| | | FIRST SKIN SCORE | SECOND SKIN SCORE |
| EST001 | 2017/5/1 8:00 | 80 | 70 |
| EST002 | 2017/5/1 22:00 | 70 | 90 |
| EST003 | 2017/5/2 7:45 | 90 | 80 |
| EST004 | 2017/5/2 22:15 | 30 | 50 |
| . | . | . | . |

FIG.11

| MACHINE INFORMATION DATABASE | | | | | | |
|---|---|---|---|---|---|---|
| MACHINE ID | OWNER USER ID | CARTRIDGE | | | | |
| | | SLOT1 | SLOT2 | SLOT3 | SLOT4 | SLOT5 |
| MA001 | U001 | CA001 80 | CA002 85 | CA003 55 | CA004 70 | CA005 20 |
| MA002 | U002 | CA002 40 | CA002 55 | CA004 55 | CA005 40 | CA006 90 |
| · | · | · | | | | · |

*FIG.12*

| RECIPE INFORMATION DATABASE | | |
|---|---|---|
| RECIPE ID | USAGE AMOUNT | CONDITION |
| REC001 | CA001=0<br>CA002=0<br>CA003=4<br>CA004=4<br>CA005=2 | 0～20 |
| REC002 | CA001=0<br>CA002=0<br>CA003=5<br>CA004=1<br>CA005=2 | 20～40 |
| REC003 | CA001=0<br>CA002=0<br>CA003=10<br>CA004=4<br>CA008=5 | 40～60 |
| . | . | . |

*FIG.18*

| RECIPE INFORMATION DATABASE | | | |
|---|---|---|---|
| RECIPE ID | USAGE AMOUNT | SCORE CONDITION | EMOTION CONDITION |
| REC001 | CA001=0<br>CA002=0<br>CA003=4<br>CA004=4<br>CA005=2 | 0〜20 | E1 |
| REC002 | CA001=0<br>CA002=0<br>CA003=5<br>CA004=1<br>CA005=2 | 20〜40 | E2 |
| REC003 | CA001=0<br>CA002=0<br>CA003=10<br>CA004=4<br>CA008=5 | 40〜60 | E3 |
| . | . | . | . |

FIG.23

| RECIPE INFORMATION DATABASE | | | | | | | |
|---|---|---|---|---|---|---|---|
| RECIPE ID | USAGE AMOUNT | MIXIER | | | HEATER | | CONDITION |
| | | MIXING SPEED | MIXING ORDER | MIXING TIME | HEATING TEMP | HEATING TIME | |
| REC001 | CA001=0 CA002=0 CA003=4 CA004=4 CA005=2 | 2 | 5 4 3 | 10 | N/A | 0 | 0~20 |
| REC002 | CA001=0 CA002=0 CA003=5 CA004=1 CA005=2 | 0 | N/A | 0 | 80 | 3 | 20~40 |
| REC003 | CA001=0 CA002=0 CA003=10 CA004=4 CA008=5 | 5 | 3 4 5 | 5 | 60 | 5 | 40~60 |
| · | · | | | | · | · | |

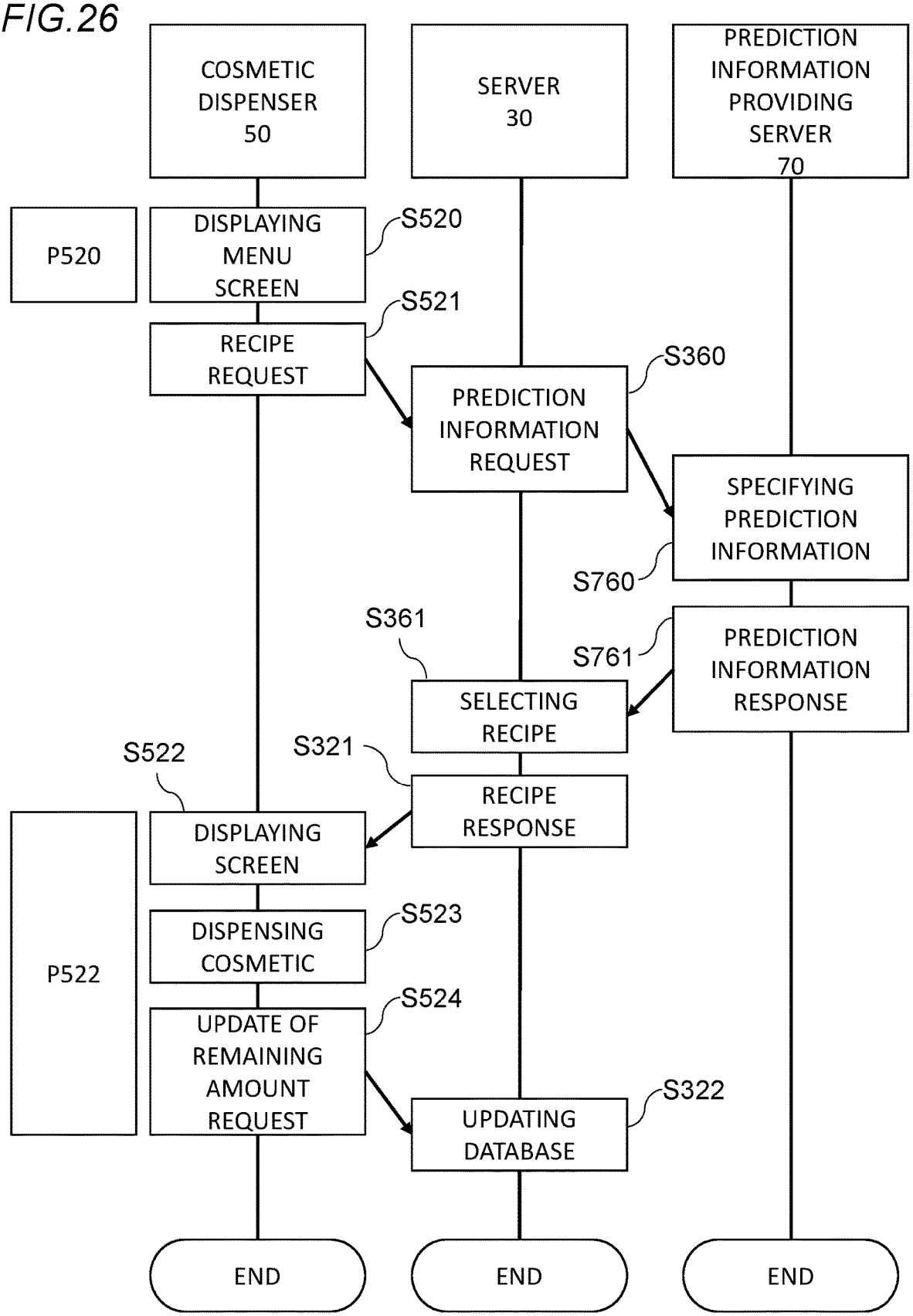

INFORMATION PROCESSING APPARATUS, PROGRAM, COSMETIC DISPENSER

TECHNICAL FIELD

The present invention relates to an information processing apparatus, a program, and a cosmetic dispenser.

BACKGROUND ART

In recent years, demand for cosmetics customized for cosmetic users (hereinafter referred to as "customized cosmetics") has increased.

For example, Patent Document 1 discloses a technology for providing customized cosmetics in accordance with a user's skin condition.

PRIOR ART DOCUMENTS

Patent Documents

[Patent Document 1] JP-T-2017-510389

SUMMARY OF INVENTION

Technical Problem

Human skin condition is affected by various factors.

For example, the environment where the user stays, the user's action, and the user's psychosomatic are known as factors that affect the skin condition.

However, since Patent Document 1 does not consider these user-unique factors, the suitability of customized cosmetics to users is insufficient.

An object of the present subject matter is to provide a customized cosmetic suitable to user-unique factors.

Solution to Problem

One aspect of the present embodiment is an information processing apparatus capable of communicating with a cosmetic dispenser configured to dispense at least one of a plurality of cosmetics based on recipe information indicating a usage amount of each of the plurality of cosmetics: the apparatus comprising:
a retrieve module configured to retrieve user-unique information unique to the user, the user-unique information including at least one of user attribute information related to the user's attributes, environmental information related to the user's environment, action information related to the user's action, and psychosomatic information related to the user's psychosomatic, skin information related to the user's skin, and information related to cosmetics which the user has used;
a selection module configured to select the recipe information based on the user unique information among a plurality of recipe information; and
a transmission module configured to transmit the selected recipe information to the cosmetic dispenser.

Advantageous Effects of Invention

According to the present embodiment, it is possible to provide a customized cosmetic suitable to the user-unique factors.

BRIEF DESCRIPTION OF DRAWINGS

FIG. 5 is a diagram showing a data structure of a user information database according to the present embodiment.

FIG. 6 is a diagram showing a data structure of an environment log information database according to the present embodiment.

FIG. 7 is a diagram showing a data structure of an action log information database according to the present embodiment.

FIG. 8 is a diagram showing a data structure of a psychosomatic log information database according to the present embodiment.

FIG. 9 is a diagram showing a data structure of a skin log information database according to the present embodiment.

FIG. 10 is a diagram showing a data structure of a skin evaluation log information database according to the present embodiment.

FIG. 11 is a diagram showing a data structure of a machine information database according to the present embodiment.

FIG. 12 is a diagram showing a data structure of a recipe information database according to the present embodiment.

FIG. 18 is a diagram illustrating a data structure of a recipe information database according to a first variation.

FIG. 23 is a diagram illustrating a data structure of a recipe information database according to a third variation.

FIG. 26 is a flowchart of a process for dispensing cosmetics according to a seventh variation.

DESCRIPTION OF EMBODIMENTS

Embodiments

Figure 1:
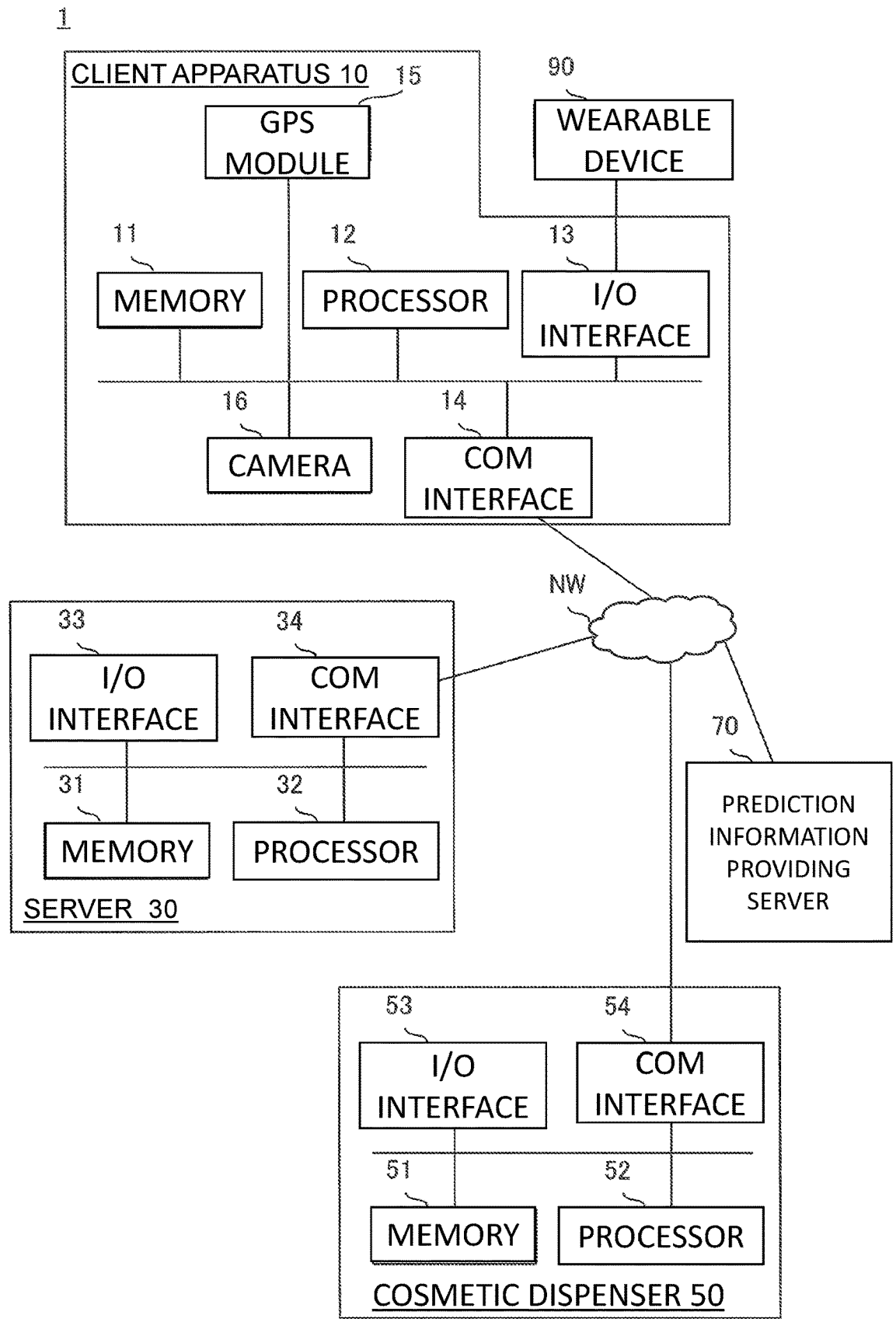
FIG. 1 is a block diagram illustrating a configuration of an information processing system according to the present embodiment.

Hereinafter, an embodiment of the present invention will be described in detail with reference to the drawings.

Note that, in the drawings for describing the embodiments, the same components are denoted by the same reference sign in principle, and the repetitive description thereof is omitted.

(1) Configuration of Information Processing System

The configuration of the information processing system will be described.

FIG. 1 is a block diagram showing the configuration of the information processing system according to the present embodiment.

As shown in FIG. 1, the information processing system 1 includes a client apparatus 10, a server 30, a cosmetic dispenser 50, a prediction information providing server 70, and a wearable device 90.

The client apparatus 10, the server 30, the cosmetic dispenser 50, and the prediction information providing server 70 are connected via a network (for example, an internet or an intranet) NW.

The client apparatus 10 is an example of an information processing apparatus that transmits a request to the server 30.

The client apparatus 10 is, for example, a smartphone, a tablet device, or a personal computer.

The server 30 is an example of an information processing apparatus that provides a response corresponding to a predetermined request to the client apparatus 10 and the cosmetic dispenser 50.

The server 30 is, for example, a web server.

The cosmetic dispenser 50 is configured to provide cosmetics based on information transmitted from the server 30.

The prediction information providing server 70 is an example of an information processing apparatus that provides prediction information indicating future prediction.

For example, the prediction information providing server 70 provides the following information:
environment prediction information indicating prediction of future environment (for example, weather prediction of a place where the user lives);
action prediction information indicating prediction of future user action (for example, a schedule arbitrarily input by the user); and
psychosomatic prediction information indicating the prediction of the user's psychosomatic (for example, the prediction date of the sexual cycle arbitrarily input by the user).

The wearable device 90 includes at least one of environment log information (FIG. 6 described later), action log information (FIG. 7 described later), and psychosomatic log information (FIG. 8 described later).

(1-1) Configuration of Client Device

The configuration of the client apparatus 10 will be described with reference to FIG. 1.

As shown in FIG. 1, the client apparatus 10 includes a memory 11, a processor 12, an input and output (hereinafter, referred to as "I/O") interface 13, a communication interface 14, a GPS module 15, and a camera 16.

The memory 11 is configured to store a program and data.

The memory 11 is, for example, a combination of a ROM (read only memory), a RAM (random access memory), and a storage (for example, a flash memory or a hard disk).

The program includes, for example, the following programs:
OS (Operating System) program; and
program of application (for example, a cosmetic dispense application linked to the cosmetic dispenser 50).

The data includes, for example, the following data:
database referenced in information processing; and
data generated by executing information processing (that is, execution result of information processing).

The processor 12 is configured to activate a program stored in the memory 11 to implement the functions of the client apparatus 10.

The processor 12 is an example of a computer.

The I/O interface 13 is configured to retrieve a user instruction from an input device connected to the client apparatus 10, retrieve information from the wearable device 90, and output information to an output device connected to the client apparatus 10.

The input device is, for example, a keyboard, a pointing device, a touch panel, or a combination thereof.

The output device is, for example, a display.

The communication interface 14 is configured to control communication between the client apparatus 10 and the server 30.

The GPS module 15 is configured to retrieve location information of the client apparatus 10 by communicating with a GPS (Global Positioning System) satellite.

The camera 16 is configured to capture an image.

The camera 16 is, for example, a CMOS (Complementary Metal Oxide Semiconductor) camera.

(1-2) Server Configuration

The configuration of the server 30 will be described with reference to FIG. 1.

As shown in FIG. 1, the server 30 includes a memory 31, a processor 32, and a communication interface 34.

The memory 31 is configured to store a program and data.

The memory 31 is, for example, a combination of ROM, RAM, and storage (for example, flash memory or hard disk).

The program includes, for example, the following programs:
OS program; and
program of application for executing information processing.

The data includes, for example, the following data:
database referred to in information processing; and
execution result of information processing.

The processor 32 is configured to activate a program stored in the memory 31 to implement the functions of the server 30.

The processor 32 is an example of a computer.

The I/O interface 33 is configured to retrieve a user instruction from an input device connected to the server 30 and output information to an output device connected to the server 30.

The input device is, for example, a keyboard, a pointing device, a touch panel, or a combination thereof.

The output device is, for example, a display.

The communication interface 34 is configured to control communication between the server 30 and the client apparatus 10.

(1-3) Configuration of Cosmetic Dispenser

The configuration of the cosmetic dispenser 50 will be described with reference to FIG. 1.

As shown in FIG. 1, the cosmetic dispenser 50 includes a memory 51, a processor 52, an I/O interface 53, and a communication interface 54.

The memory 51 is configured to store a program and data.

The memory 51 is, for example, a combination of ROM, RAM, and storage (for example, flash memory or hard disk).

The program includes, for example, the following programs:
OS program;
firmware program for controlling cosmetic dispenser 50;
OS program; and
program of application for executing information processing.

The data includes, for example, the following data:
database referred to in information processing; and
data acquired by executing information processing (that is, execution result of information processing)

Processor 52 is configured to activate a program stored in the memory 51 to realize the functions of the cosmetic dispenser 50.

The processor 52 is an example of a computer.

The I/O interface 53 is configured to receive a user instruction from the input device of the cosmetic dispenser 50 or the client apparatus 10, and output information to the output device of the cosmetic dispenser 50.

The input device is, for example, a touch panel.

The output device is, for example, a display.

The communication interface 54 is configured to control communication between the cosmetic dispenser 50 and the server 30.

The structure and configuration of the cosmetic dispenser of the present embodiment will be described.

Figure 2:
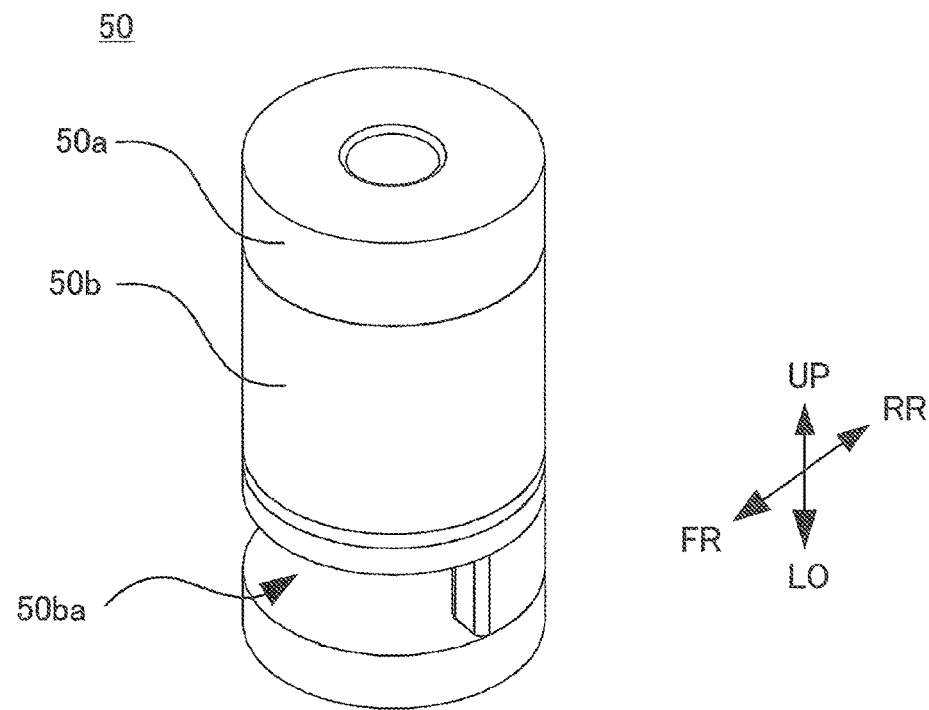
FIG. 2 is a diagram illustrating a structure of the cosmetic dispenser of FIG. 1.
Figure 2:
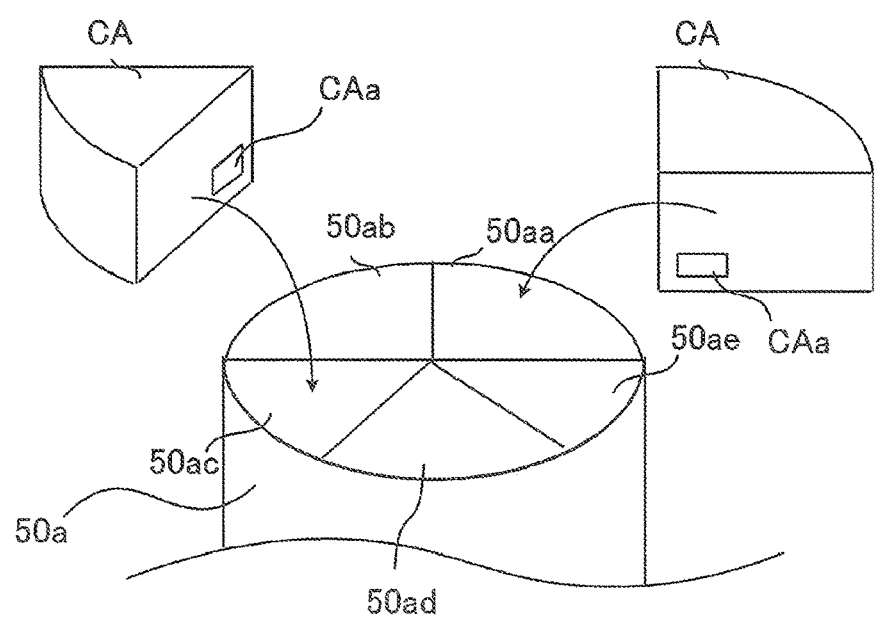

FIG. 2 is a diagram illustrating the structure of the cosmetic dispenser of FIG. 1.

Figure 3:
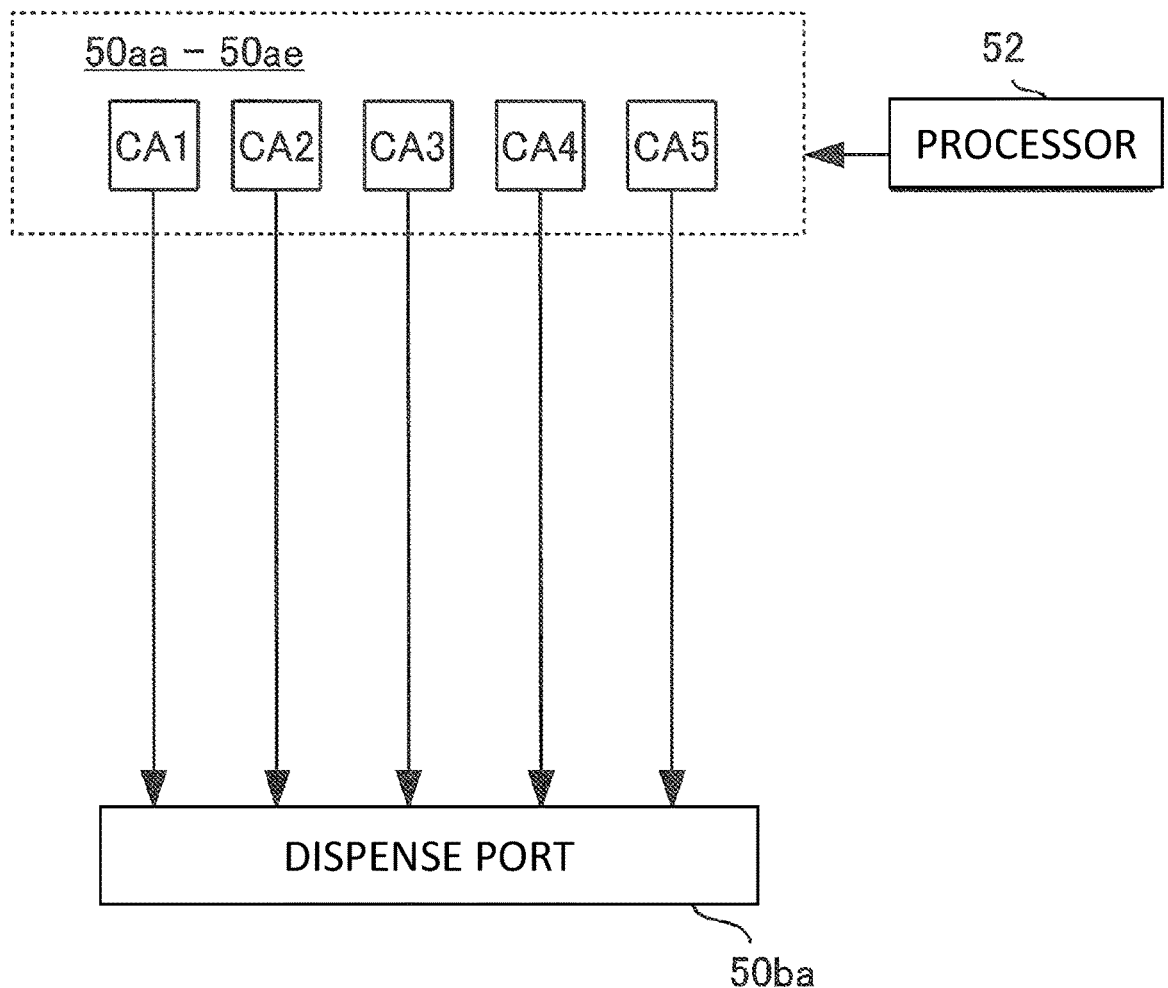
FIG. 3 is a schematic diagram showing a configuration of the cosmetic dispenser of FIG. 1.

FIG. 3 is a schematic diagram showing a configuration of the cosmetic dispenser of FIG. 1.

As shown in FIG. 2A, the cosmetic dispenser 50 includes an upper part 50*a* and a lower part 50*b*.

A dispense port 50*ba* is disposed in the lower part 50*b*.

The dispense port 50*ba* opens toward the front FR.

As shown in FIG. 2B, a plurality of cartridge slots 50*aa* to 50*ae* are disposed inside the upper part 50*a*.

A cartridge CA is detachably held in each of the cartridge slots 50*aa* to 50*ae*.

Each cartridge CA contains cosmetics (for example, liquid).

The cosmetic contained in each cartridge CA may be used without being mixed with cosmetics contained in other cartridges CA and may be mixed with the cosmetics contained in other cartridges CA.

An IC chip CAa is disposed on the side surface of each cartridge CA.

The IC chip CAa stores information related to the cartridge CA (hereinafter referred to as "cartridge information").

The cartridge information includes, for example, the following information:
cartridge ID for identifying the cartridge;
remaining value of the cosmetics contained in the cartridge; and
information indicating the cosmetics contained in the cartridge.

As shown in FIG. 3, each of the cartridge slots 50*aa* to 50*ae* holds the cartridges CA1 to CA5.

Different types of cosmetics are contained in the cartridges CA1 to CA5.

The processor 52 controls the cartridges CA1 to CA5 to dispense the cosmetics contained in the cartridges CA1 to CA5 from the dispense port 50*ba*.

(2) Summary of Present Embodiment

A summary of the present embodiment will be described.

Figure 4:
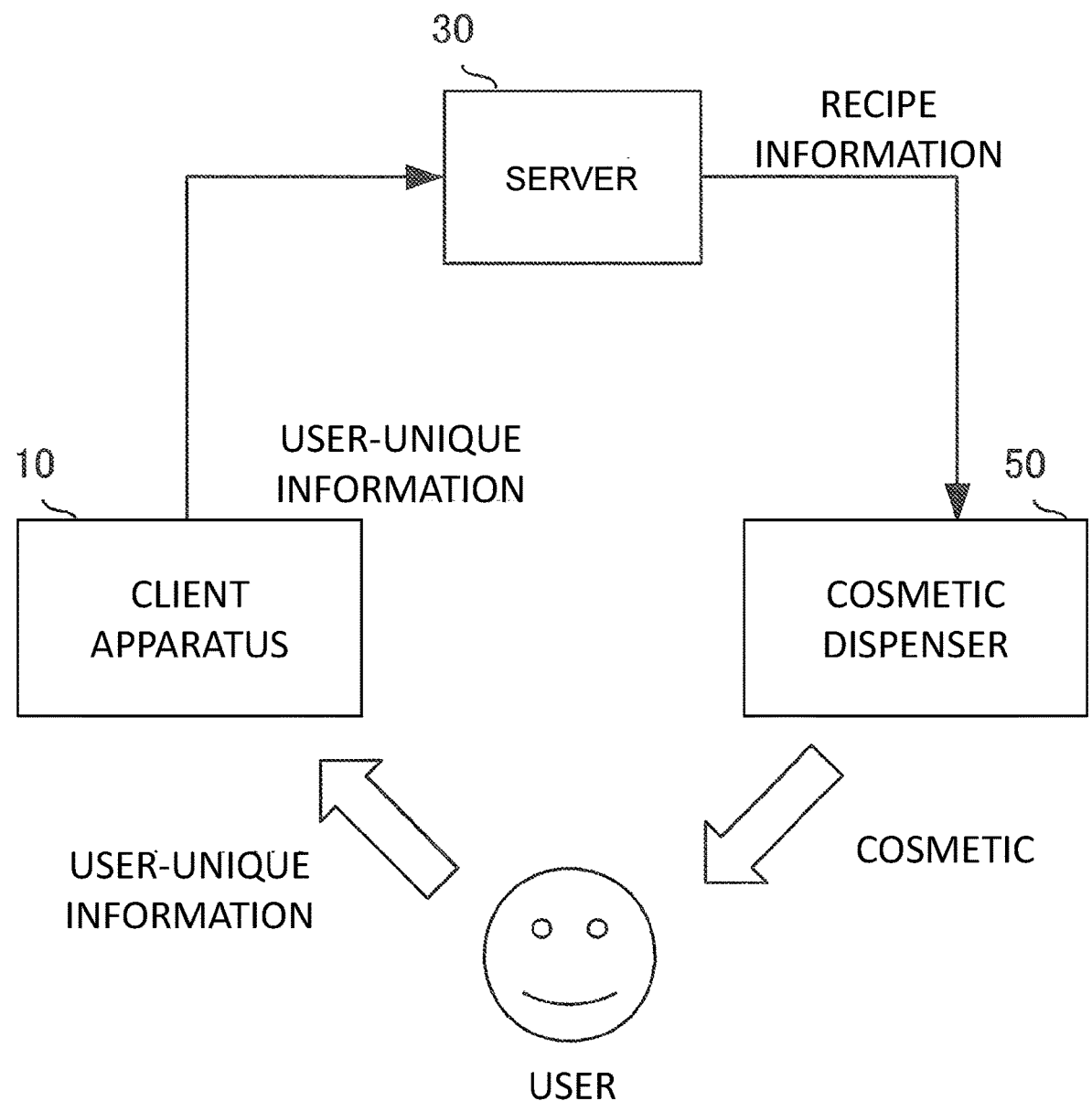
FIG. 4 is a schematic view of the present embodiment.

FIG. 4 is a schematic diagram of the present embodiment.

As shown in FIG. 4, in the present embodiment, a user (for example, a consumer of cosmetics) uses a client apparatus 10 and a cosmetic dispenser 50.

The client apparatus 10 retrieves information unique to the user (hereinafter referred to as "user unique information") from the user.

The client apparatus 10 transmits the retrieved user unique information to the The user unique information includes user log information and prediction information.

The user log information is information indicating at least one history of the user's past environmental information, action information, psychosomatic information, skin information, and skin evaluation information.

The prediction information is information indicating at least one prediction of the user's future environment, action, and psychosomatic.

The server 30 selects recipe information to be transmitted to the cosmetic dispenser 50 among a plurality of recipe information based on the user unique information transmitted from the client apparatus 10.

The server 30 transmits the selected recipe information to the cosmetic dispenser 50.

The cosmetic dispenser 50 provides cosmetics based on the recipe information transmitted from the server 30 to the user.

Recipe information is based on user-unique information.

That is, the cosmetics provided to the user are customized according to the factors specific to the user.

(3) Database

The database of the present embodiment will be described.

The following database is stored in the memory 31.

(3-1) User Information Database

The user information database of the present embodiment will be described.

FIG. 5 is a diagram illustrating a data structure of the user information database according to the present embodiment.

The user information database shown in FIG. 5 stores information related to users (hereinafter referred to as "user information").

The user information database includes a "user ID" field, a "user name" field, a "user attribute" field, an "estimation formula" field, a "used cosmetic ID" field, and an "inquiry" field.

Each field is associated with each other.

The "user ID" field stores a user ID for identifying the user.

The "user name" field stores information (for example, text) indicating the user name.

The "user attribute" field stores information related to user attributes (hereinafter referred to as "user attribute information").

The user attribute information is information arbitrarily determined by the user.

The "user attribute" field includes a "gender" field, an "age" field, and an "address" field.

The "gender" field stores information indicating the gender of the user.

The "age" field stores information indicating the age of the user.

The "address" field stores information indicating the address of the user.

The "estimation formula" field stores an estimation formula (formula 1) for estimating the skin condition of the user.

The estimation formula includes a coefficient for each factor that affects the user's skin.

$$f = a \times A + b \times B + c \times C + d \times D \quad \text{(Equation 1)}$$

f ... Score indicating the estimation result of skin condition (hereinafter referred to as "skin score");
a ... Environmental coefficient;
A ... Environmental information;
b ... action Coefficient;
B ... Behavior information;
c ... Psychosomatic coefficient;
C ... Psychosomatic information;
d ... Skin coefficient; and
D ... Skin information.

An estimation formula is prepared for each user's skin condition index (hereinafter referred to as "skin index").

That is, the coefficient included in the estimation formula is different for each skin index.

The skin index is, for example, at least one of the following:
moisture content of the stratum corneum;
skin texture;
skin color;
dry skin;
skin smoothness;
skin transparency;
degree of skin whitening;
skin roughness;
degree of skin inflammation; and
degree of skin wrinkles.

The "used cosmetic ID" field stores a cosmetic ID for identifying the cosmetic which the user has used.

The "inquiry" field stores information indicating the user's answer to the question related to the user's skin.

(3-2) Environmental Log Information Database

The environmental log information database of the present embodiment will be described.

FIG. 6 is a diagram illustrating a data structure of the environment log information database according to the present embodiment.

The environment log information database of FIG. 6 stores information (hereinafter referred to as "environment log information") indicating a log of environment information related to the environment spent by the user.

The environment log information is information acquired from the wearable device 90.

The environmental log information database includes an "environment log ID" field, a "date and time" field, an "UV exposure amount" field, a "temperature" field, and a "humidity" field.

Each field is associated with each other.

The environment log information database is associated with the user ID.

The "environment log ID" field stores an environment log ID for identifying environment information constituting the environment log information.

The "date and time" field stores information indicating the date and time when the environment information was acquired.

The "UV exposure amount" field stores information indicating the amount of ultraviolet rays that the user has taken (hereinafter referred to as "UV exposure amount").

The "temperature" field stores information indicating the temperature of the environment spent by the user.

The "humidity" field stores information indicating the humidity of the environment spent by the user.

(3-3) Action Log Information Database

The action log information database of the present embodiment will be described.

FIG. 7 is a diagram illustrating a data structure of the action log information database according to the present embodiment.

The action log information database shown in FIG. 7 stores information (hereinafter referred to as "action log information") indicating a history of action information relating to user action.

The action log information is information retrieved from the wearable device 90, information determined according to a user instruction (for example, a user's answer to a questionnaire), or a combination thereof.

The action log information database includes an "action log ID" field, a "date and time" field, an "action" field, a "start time" field, an "end time" field, a "calorie change" field, and a "location" field.

Each field is associated with each other.

The action log information database is associated with the user ID.

The "action log ID" field stores an action log ID for identifying action information constituting the action log information.

The "date and time" field stores information indicating the date and time when the action information is retrieved.

The "action" field stores information related to the user's action.

The user action includes at least one of the following:
meals (for example, the contents of meals);
exercise (for example, the event of exercise); and
sleep (for example, the number of wake-ups during sleep).

The "start time" field stores information indicating the start time of the action.

The "end time" field stores information indicating the end time of the action.

The "calorie change" field stores information indicating calorie intake or calorie consumption (an example of energy consumption) corresponding to the action.

The "location" field stores the location information acquired by the GPS module 15.

(3-4) Psychosomatic Log Information Database

The psychosomatic log information database of the present embodiment will be described.

FIG. 8 is a diagram showing a data structure of the psychosomatic log information database of the present embodiment.

The psychosomatic log information database shown in FIG. 8 stores information indicating the history of psychosomatic information related to the user's psychosomatic (hereinafter referred to as "psychosomatic information").

The psychosomatic log information is information determined according to information acquired from the wearable device 90, a user instruction (for example, a user's answer to an inquiry (hereinafter referred to as "inquiry result")), or a combination thereof.

The psychosomatic log information database includes a "psychosomatic log ID" field, a "date and time" field, a "pulse value" field, a "estrous cycle" field, a "stress" field, and a "mindfulness" field.

Each field is associated with each other.

The psychosomatic log information database is associated with the user ID.

The "psychosomatic log ID" field stores a psychosomatic log ID for identifying psychosomatic information constituting the psychosomatic log information.

The "date and time" field stores information indicating the date and time when psychosomatic information is acquired.

The "pulse value" field stores the pulse value of the user.

The pulse value is information acquired from the wearable device 90, for example.

The "sexual cycle" field stores information indicating an sexual cycle (an example of hormone balance information).

The "stress" field stores stress information indicating an index of stress.

The stress information indicates, for example, the intensity of stress, the factor of stress, the type of stress, or a combination thereof.

The stress information is determined by the pulse value, the sexual cycle, the interview result, or a combination thereof.

The "mindfulness" field stores mindfulness information indicating a user's mindfulness index.

Mindfulness information is determined by the pulse value, the estrous cycle, the interview result, or a combination thereof.

(3-5) Skin Log Information Database

The skin log information database of the present embodiment will be described.

FIG. 9 is a diagram showing a data structure of the skin log information database of the present embodiment.

The skin log information database in FIG. 9 stores information (hereinafter referred to as "skin log information") indicating a history of skin information related to the user's skin.

The skin log information database includes a "skin log ID" field, a "date and time" field, a "skin image" field, a "skin color" field, a "water content" field, and a "sebum amount" field.

Each field is associated with each other.

The skin log information database is associated with the user ID.

The "skin log ID" field stores a skin log ID for identifying skin log information.

The "date and time" field stores information indicating the date and time when the skin information is acquired.

The "skin image" field stores image data of the user's skin image.

The "skin color" field stores information (for example, RGB values) indicating the skin color estimated from the user's skin image.

The "water content" field stores information indicating a water content index estimated from the user's skin image.

The "sebum amount" field stores information indicating an index of the sebum amount estimated from the user's skin image.

(3-6) Skin Evaluation Log Information Database

The skin evaluation log information database of the present embodiment will be described.

FIG. 10 is a diagram illustrating a data structure of the skin evaluation log information database according to the present embodiment.

The skin evaluation log information database of FIG. 10 stores information (hereinafter referred to as "skin evaluation log information") indicating a history of qualitative evaluation (hereinafter referred to as "skin evaluation") related to the skin condition.

The skin evaluation log information database includes a "skin evaluation log ID" field, a "date and time" field, and a "skin score" field.

Each field is associated with each other.

The skin evaluation log information database is associated with the user ID.

The "skin evaluation log ID" field stores a skin evaluation log ID for identifying the skin evaluation constituting the skin evaluation log information.

The "date and time" field stores information indicating the date and time when the skin evaluation is generated.

The "skin score" field stores a skin score acquired by applying user log information (at least one of environment log information, action log information, psychosomatic log information, and skin log information) to the estimation formula.

The "skin score" field includes a "first skin score" field and a "second skin score" field.

The "first skin score" field stores a first skin score (an example of a first skin index).

The first skin score indicates a current skin state estimated from user log information (for example, when user log information is acquired).

The "second skin score" field stores a second skin score (an example of a second skin index).

A second skin score indicates the skin state of the future estimated from user log information and prediction information (for example, one week after the day when user log information was acquired).

(3-7) Machine Information Database

The machine information database of the present embodiment will be described.

FIG. 11 is a diagram illustrating a data structure of the machine information database according to the present embodiment.

The machine information database of FIG. 11 stores information related to the cosmetic dispenser 50 (hereinafter referred to as "machine information").

The machine information database includes a "machine ID" field, an "owner user ID" field, and a "cartridge" field.

Each field is associated with each other.

The "machine ID" field stores a machine ID for identifying the cosmetic dispenser 50.

The information in the "machine ID" field is, for example, a serial number assigned in advance to the cosmetic dispenser 50.

The "owner user ID" field stores the user ID of the user who uses the cosmetic dispenser 50.

The "cartridge" field includes "slot 1" to "slot 5" fields.

The "slot 1" to "slot 5" fields store cartridge information relating to the cartridges CA1 to CA5 held in the cartridge slots 50aa to 50ae, respectively.

The cartridge information includes a cartridge ID for identifying the cartridge CA, and a remaining amount value of the cosmetics contained in the cartridge CA, and information indicating the cosmetics contained in the cartridge CA.

(3-8) Recipe Information Database

The recipe information database of the present embodiment will be described.

FIG. 12 is a diagram illustrating a data structure of the recipe information database according to the present embodiment.

Recipe information database of FIG. 12 stores the recipe information.

The recipe information indicates a method for customizing cosmetics.

The recipe information database includes a "recipe ID" field, a "usage amount" field, and a "condition" field.

Each field is associated with each other.

The "recipe ID" field stores a recipe ID for identifying recipe information.

Information in the "recipe ID" field is determined by the server 30.

The "usage amount" field stores information indicating the usage amount of each cosmetic.

The "condition" field stores information indicating the range of the skin score as a reference when selecting recipe information.

(4) Information Processing

Information processing according to the present embodiment will be described.

Figure 13:
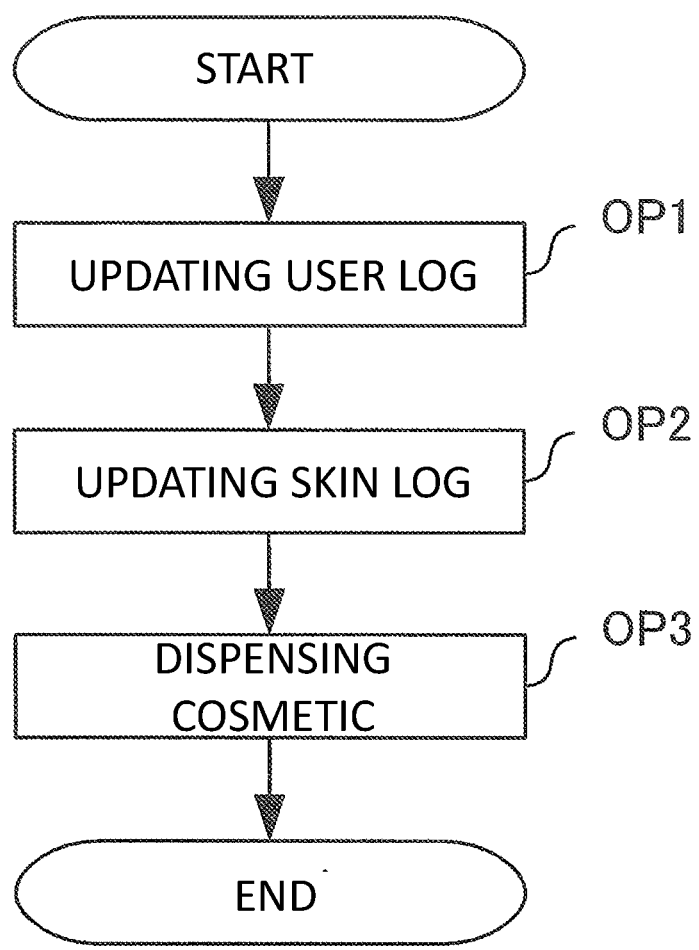
FIG. 13 is a diagram illustrating an overall flow of information process according to the present embodiment.

FIG. 13 is a diagram illustrating an overall flow of information processing according to the present embodiment.

As shown in FIG. 13, the information processing according to the present embodiment includes updating the user log (OP1), updating the skin log (OP2), and dispensing cosmetics (OP3).

(4-1) User Log Update Processing

The process for updating user log of the present embodiment will be described.

Figure 14:
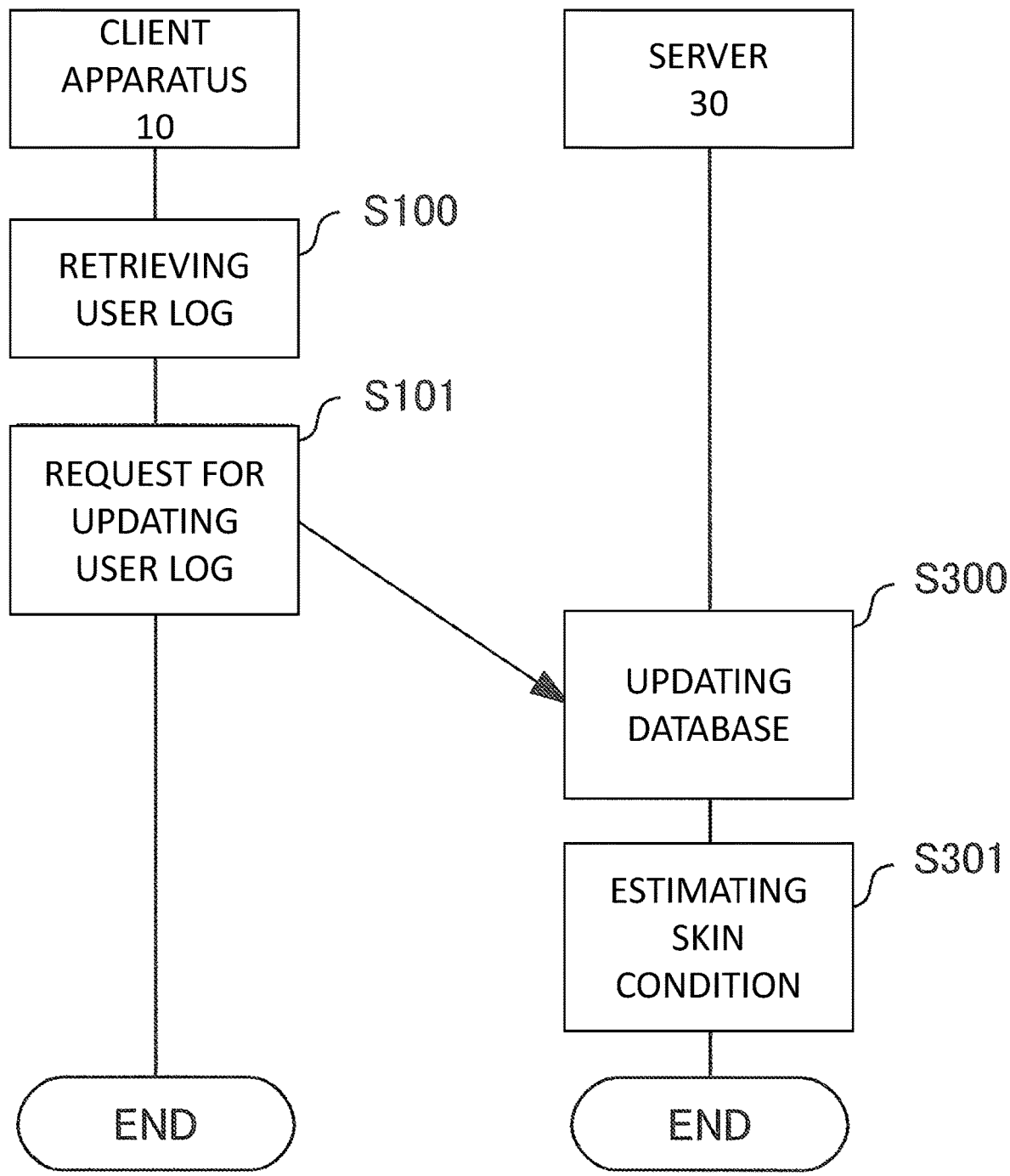
FIG. 14 is a flowchart of process for updating user log according to the present embodiment.

FIG. 14 is a flowchart of process for updating user log according to the present embodiment.

Of the steps in FIG. 14, the step executed by the client apparatus 10 is executed as a function of the cosmetic dispense application.

As shown in FIG. 14, the client apparatus 10 executes retrieving user log (S100).

Specifically, the processor 12 retrieves user log information (at least one of environment log information, action log information, and psychosomatic log information) from the wearable device 90 via the I/O interface 13.

After step S100, the client apparatus 10 executes a user log update request (S101).

Specifically, the processor 12 transmits user log update request data to the server 30.

The user log update request data includes the following information:

user ID; and information indicating date and time of execution of step S101.

User log information acquired in step S100 After step S101, the server 30 executes updating database (S300) based on user log update request data.

As a first example, when the user log update request data includes environment log information, the processor 32 adds a new record into the environment log information database (FIG. 6) associated with the user ID included in the user log update request data transmitted in step S101.

The following information is stored in each field of the new record:

in the "environment log ID" field, a new environment log ID is stored;

in the "date and time" field, information indicating the execution date and time of step S101 included in the user log update request data is stored; and in the "UV exposure amount" field, the "temperature" field, and the "humidity" field, environment information included in the user log update request data is stored.

As a second example, when the user log update request data includes the action log information, the processor 32 adds a new record into the action log information database (FIG. 7) associated with the user ID included in the user log update request data transmitted in step S101.

The following information is stored in each field of the new record:

in the "action log ID" field, a new action log ID is stored;

in the "date and time" field, information indicating the execution date and time of step S101 included in the user log update request data is stored; and in the "action" field, the "start time" field, the "end time" field, the "calorie change" field, and the "location" field, action information included in the user log update request data is stored.

As a third example, when the user log update request data includes psychosomatic log information, the processor 32 adds a new record into the psychosomatic log information database (FIG. 8) associated with the user ID included in the user log update request data transmitted in step S101.

The following information is stored in each field of the new record:

in the "psychosomatic log ID" field, a new psychosomatic log ID is stored;

in the "date and time" field, information indicating the execution date and time of step S101 included in the user log update request data is stored; and in the "pulse value" field, the "estrous cycle" field, the "stress" field, and the "mindfulness" field, psychosomatic information included in the user log update request data is stored.

Thereby, the user log information is updated.

After step S300, the server 30 executes estimating skin condition (S301).

Specifically, the processor 32 refers to the user information database (FIG. 5) and specifies an estimation formula associated with the user ID included in the user log update request data.

The processor 32 calculates the skin score based on the user log information by applying the user log information updated in step S300 to the specified estimation formula.

The processor 32 stores information indicating the calculated skin score in the "first skin score" field of the skin evaluation log information database (FIG. 10) associated with the user ID.

(4-2) Skin Log Update Processing

The skin log update processing of the present embodiment will be described.

Figure 15:
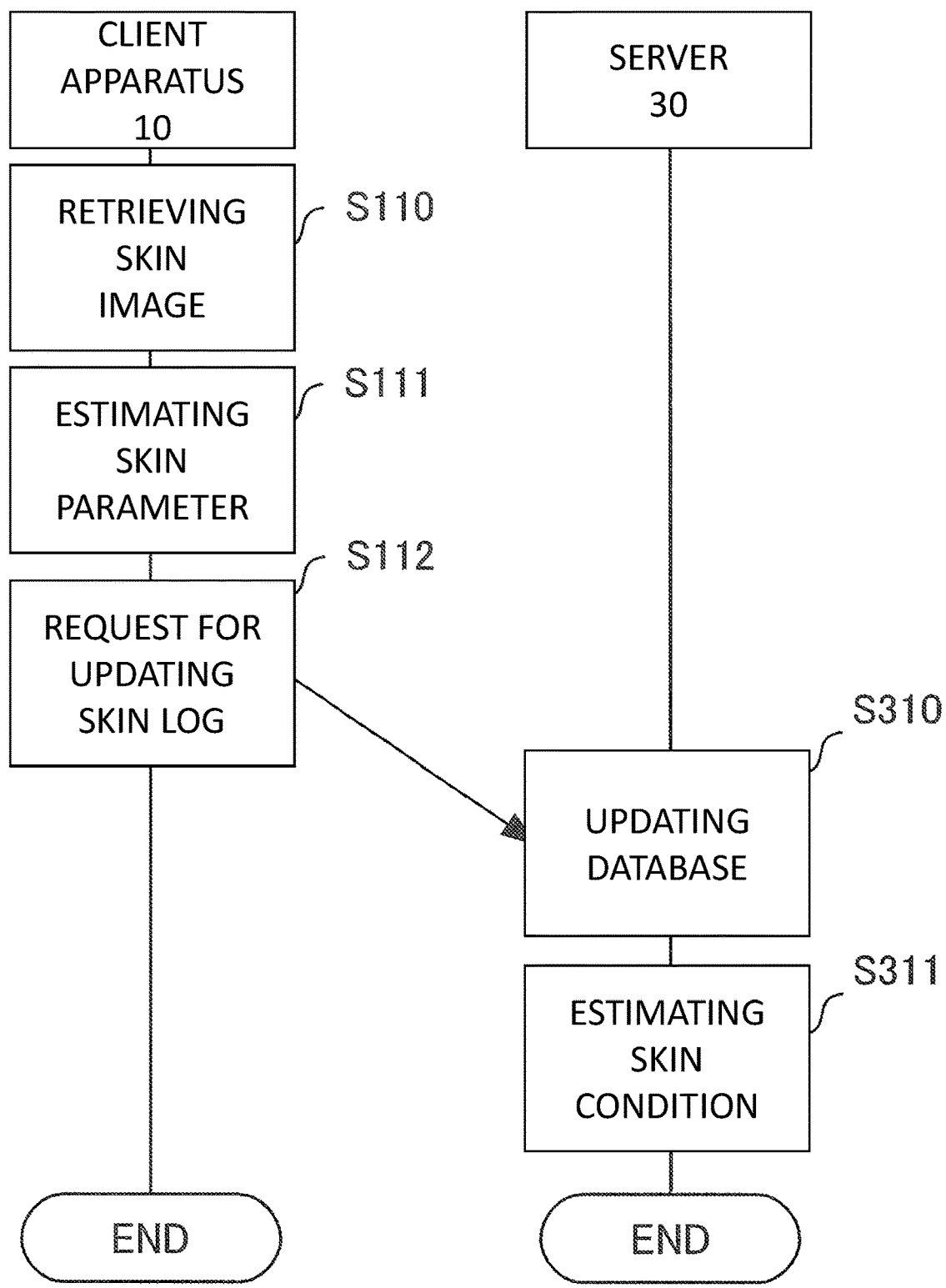
FIG. 15 is a flowchart of process for updating user log according to the embodiment.

FIG. 15 is a flowchart of process for updating user log according to the present embodiment.

Of the steps in FIG. 15, the step executed by the client apparatus 10 is executed as a function of the cosmetic dispense application.

As shown in FIG. 15, the client apparatus 10 executes retrieving skin image (S110).

Specifically, the camera 16 captures an image of the user's skin.

The processor 12 stores the captured image in the memory 11.

After step S110, the client apparatus 10 executes estimating skin parameter (S111).

The processor 12 analyzes the image stored in the memory 11 in step S110.

The processor 12 calculates a user's skin color value, a moisture content value, and a sebum amount value by applying a predetermined algorithm to the analysis result of the image.

After step S111, the client apparatus 10 executes a skin log update request (S112).

Specifically, the processor 12 transmits skin log update request data to the server 30.

The skin log update request data includes the following information:
user ID;
information indicating the execution date and time of step S112;
image data of the image captured in step S110; and
skin color value, sebum amount value, and moisture amount value calculated in step S111.

After step S112, the server 30 executes updating database (S310) based on the skin log update request data.

Specifically, the processor 32 adds a new record to the skin log information database (FIG. 9) associated with the user ID included in the skin log update request data transmitted in step S112.

The following information is stored in each field of the new record;
in the "skin log ID" field, a new skin log ID is stored.
in the "date and time" field, information indicating the execution date and time of step S112 included in the skin log update request data is stored;
in the "skin image" field, image data included in the skin log update request data is stored;
in the "skin color" field, the value of the skin color included in the skin log update request data is stored;
in the "water content" field, the value of the water content included in the skin log update request data is stored; and
in the "sebum amount" field, the value of the sebum amount included in the skin log update request data is stored.

Thereby, the skin log information is updated.

After step S310, the server 30 executes estimating skin condition (S311).

Specifically, the processor 32 refers to the user information database (FIG. 5) and specifies an estimation formula associated with the user ID included in the skin log update request data.

The processor 32 calculates the skin score based on the skin log information by applying the skin log information updated in step S310 to the specified estimation formula.

The processor 32 stores information indicating the calculated skin score in the "first skin score" field of the skin evaluation log information database (FIG. 10) associated with the user ID.

(4-3) Cosmetic Dispense Processing

The cosmetic dispense processing of the present embodiment will be described.

Figure 16:
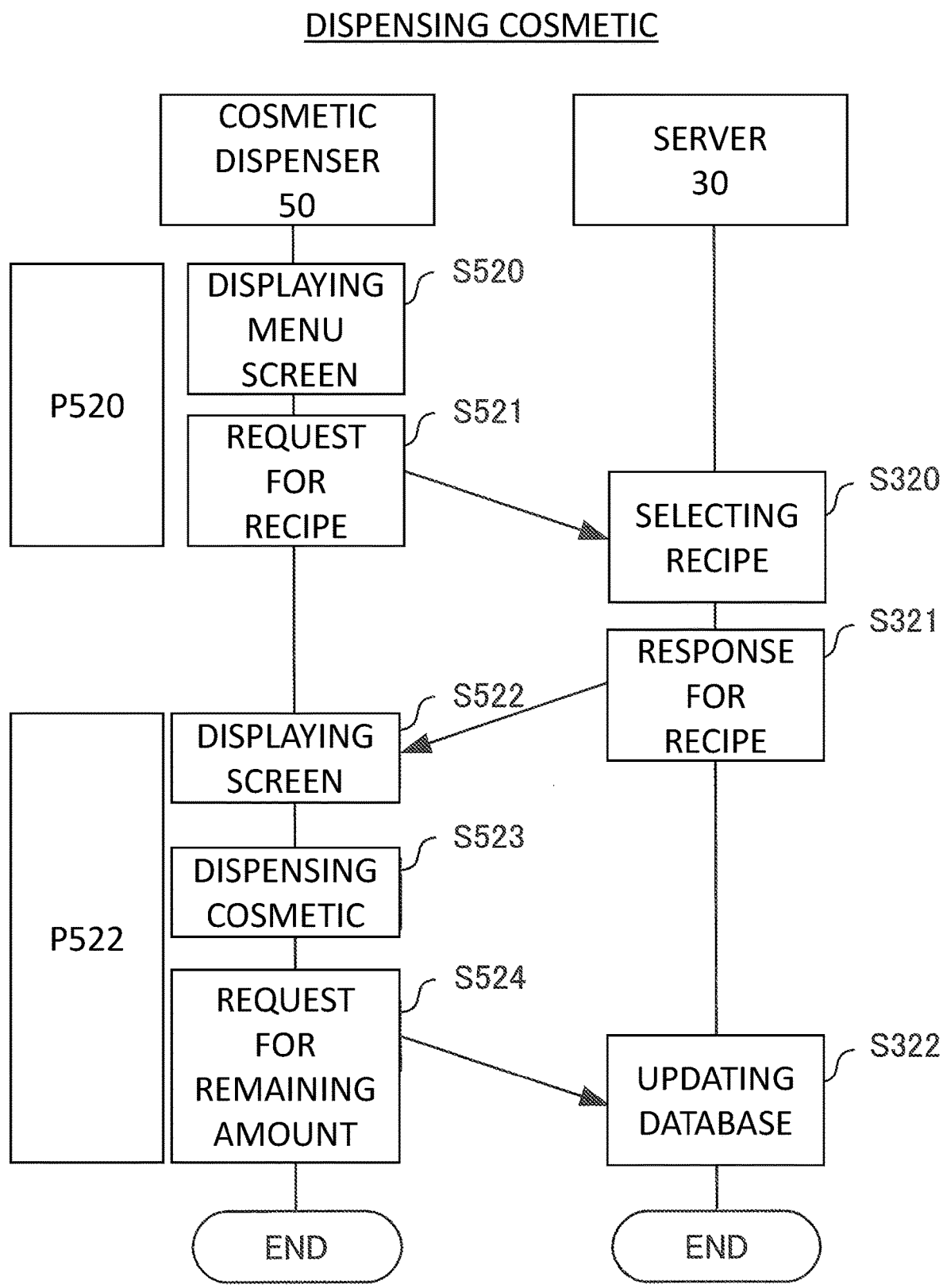
FIG. 16 is a flowchart of a process for dispensing cosmetics according to the present embodiment.

FIG. 16 is a flowchart of the process of dispensing cosmetics according to the present embodiment.

Figure 17:
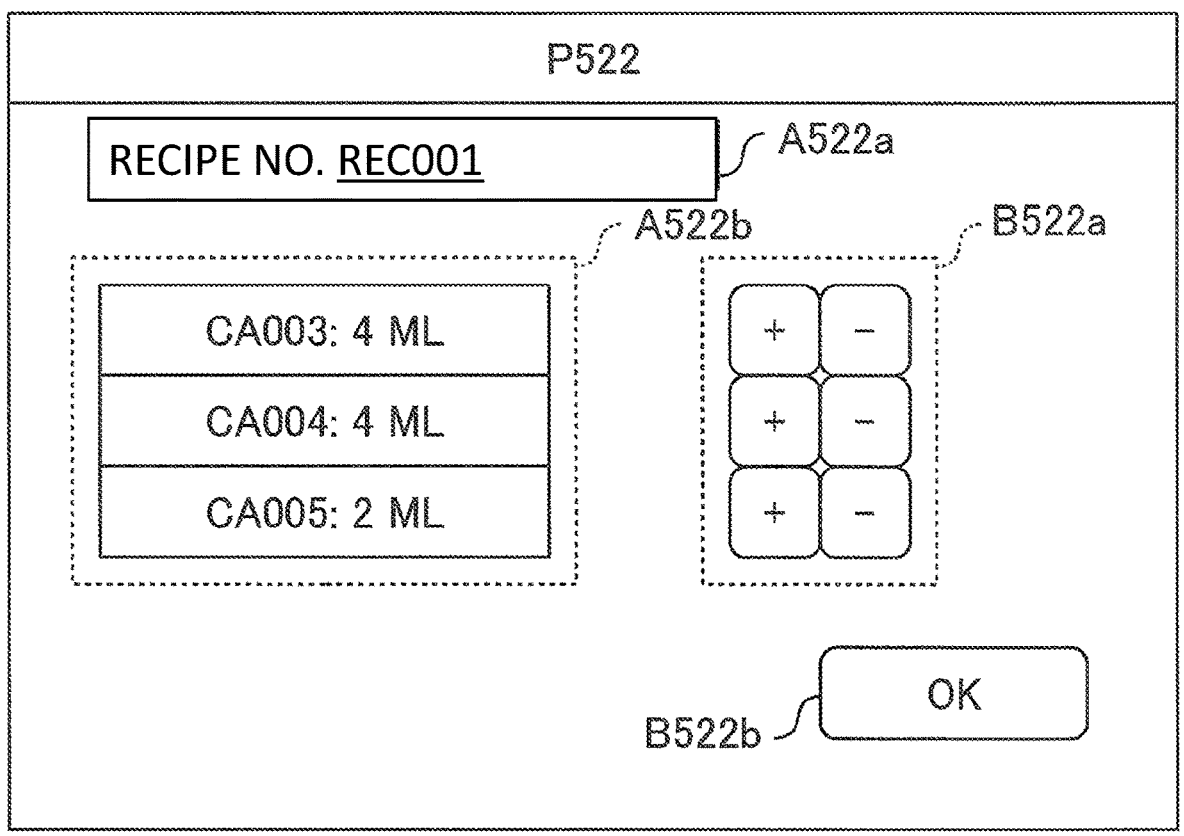
FIG. 17 is a diagram showing an example of a screen displayed in the information processing of FIG. 16.

FIG. 17 is a diagram of a screen example displayed in the information processing of FIG. 16.

As shown in FIG. 16, the cosmetic dispenser 50 executes displaying menu screen (S520).

Specifically, the processor 52 displays the screen P520 on the display.

The screen P520 displays a button object B520.

The button object B520 is an object that receives a user instruction for dispense of cosmetics.

After step S520, cosmetic dispenser 50 executes a recipe request (S521).

Specifically, when the user operates the button object B520, the processor 52 transmits recipe request data to the server 30.

The recipe request data includes the machine ID of the cosmetic dispenser 50.

After step S521, the server 30 executes selecting recipe (S320) based on the recipe request data.

Specifically, the processor 32 refers to the machine information database (FIG. 11) and specifies the owner user ID associated with the machine ID included in the recipe request data.

The processor 32 refers to the skin evaluation log information database (FIG. 10) associated with the specified owner user ID, and specifies the latest skin score (for example, the first skin score of the record including the information indicating the latest date and time stored in the "date and time" field).

The processor 32 refers to the recipe information database (FIG. 12) and specifies a record in which the specified skin score is included in the range indicated by the information in the "condition" field.

The processor 32 specifies the recipe ID and the usage amount of each cosmetic of the specified record.

After step S320, the server 30 executes a recipe response (S321).

Specifically, the processor 32 transmits recipe response data to the cosmetic dispenser 50.

The recipe response data includes the following information:
recipe ID specified in step S320; and
usage amount of each cosmetic specified in step S320

After step S321, the cosmetic dispenser 50 executes displaying screen (S522) based on the recipe response data.

Specifically, the processor 52 displays the screen P522 on the display.

The screen P522 includes display objects A522a to A522b and button objects B522a to B522b.

In the display object A522a, the recipe ID included in the recipe response data is displayed.

In the display object A522b, the usage amount of each cosmetic included in the recipe response data is displayed.

The button object B522a is an object that receives a user instruction to increase or decrease the usage amount of each cosmetic shown in the display object A522b.

The button object B522b is an object that receives a user instruction to determine the usage amount of each cosmetic shown in the display object A522b.

After step S522, the cosmetic dispenser 50 executes discharging cosmetic (S523).

Specifically, when the user operates the button object B522b, the processor 52 controls each of cartridges CA1 to CA5 so that each cosmetic contained in each of the cartridges CA1 to CA5 is dispensed by the amount used for each cosmetic shown in the display object A522b.

The cosmetic contained in each of the cartridges CA1 to CA5 is dispensed from the dispense port 50ba.

The user receives the dispensed cosmetic by inserting the user's hand into the dispense port 50ba.

Thereby, the customized cosmetics suitable for the user-unique factors may be provided to the user.

After step S524, cosmetic dispenser 50 executes a remaining amount update request (S524).

Specifically, the processor 52 transmits remaining amount update request data to the server 30.

The remaining amount update request data includes the following information:
machine ID; and
value indicating the dispense amount of the cosmetic dispensed in step S523

After step S524, the server 30 executes updating database (S322).

Specifically, the processor 32 refers to the machine information database (FIG. 11) and specifies a record including the machine ID included in the remaining amount update request data.

The processor 32 subtracts the value of the dispense amount included in the remaining amount update request data from the value of the "cartridge" field of the specified record.

As a result, the remaining amount of cosmetics contained in each of the cartridges CA1 to CA5 is stored in the server 30.

According to the present embodiment, it is possible to provide a customized cosmetic suitable for the user-unique factors.

(5) Variation

Variations of the present embodiment will be described.

(5-1) First Variation

A first variation will be described.

The first variation is an example in which a recipe is selected in consideration of a user's emotion when receiving cosmetics.

(5-1-1) Recipe Information Database

A recipe information database according to the first variation will be described.

FIG. 18 is a diagram illustrating a data structure of a recipe information database according to the first variation.

As shown in FIG. 18, the recipe information database of the first variation includes an "emotion condition" field in addition to the fields of FIG. 12.

The "emotion condition" field stores an emotion code that is a reference in selecting recipe information.

The emotion code is information indicating the user's emotion.

(5-1-2) Processing for Dispensing Cosmetics

The processing for dispensing cosmetics according to the first variation will be described.

Figure 19:
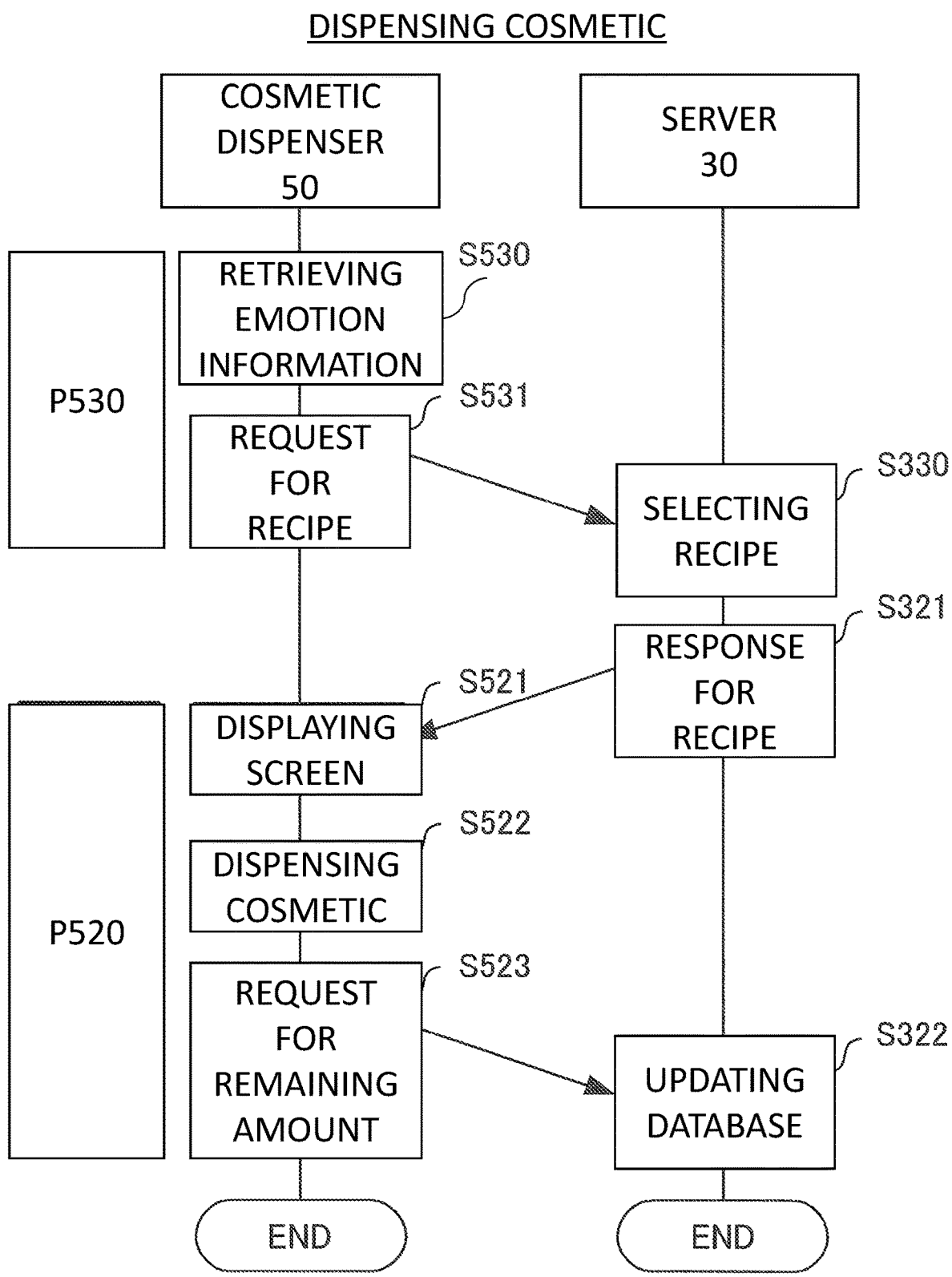
FIG. 19 is a flowchart of a process for dispensing cosmetics according to a first variation.

FIG. 19 is a flowchart of a process for dispensing cosmetics according to the first variation.

Figure 20:
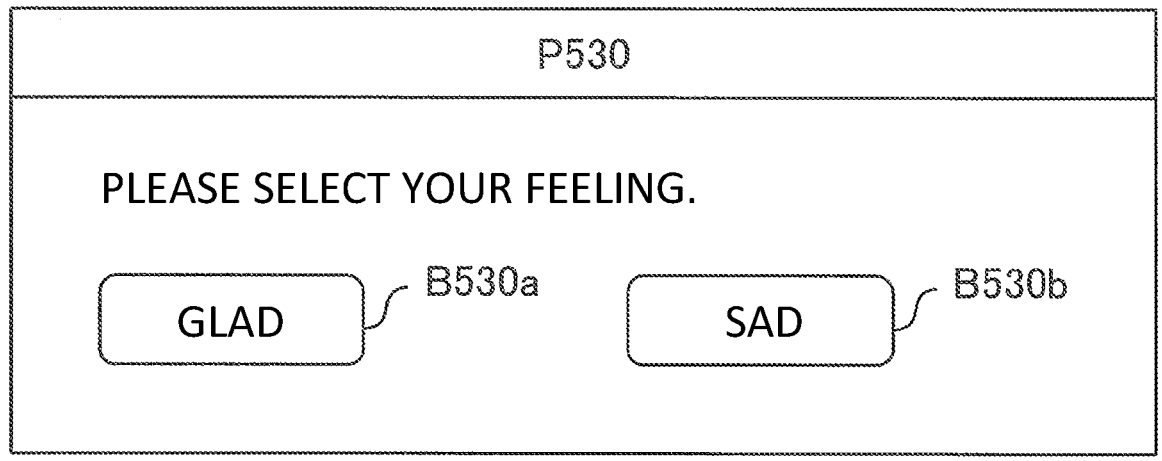
FIG. 20 is a diagram of an example of screen displayed in the information processing of FIG. 19.
Figure 20:
Figure 20:
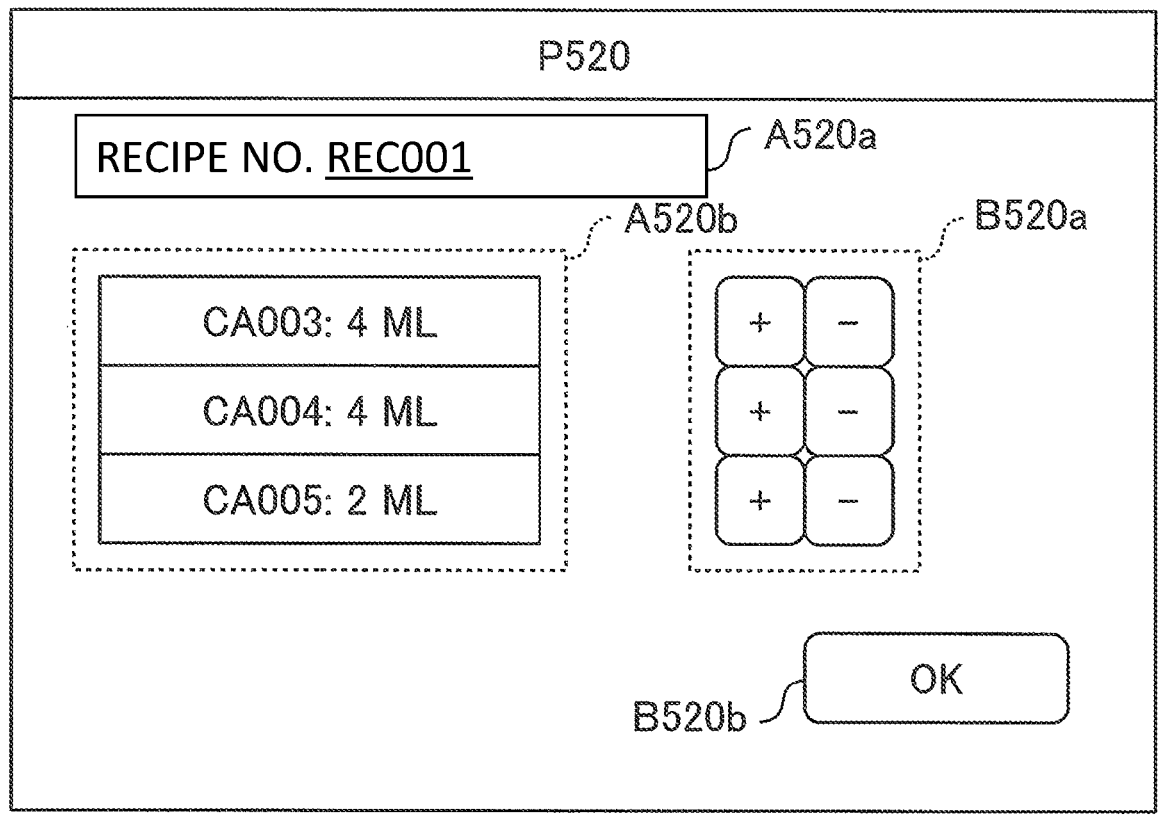
Figure 20:

FIG. 20 is a diagram of a screen example displayed in the information processing of FIG. 19.

As shown in FIG. 19, the cosmetic dispenser 50 executes retrieving emotion information (S530).

Specifically, when the user operates the button object B520, the processor 52 displays the screen P530 on the display.

The screen P530 includes button objects B530a to B530b.

The button objects B530a to B530b are objects that receive designation of user emotions.

Codes indicating emotions are assigned to the button objects B530a to B530b.

When the user operates the button object B530a, the processor 52 receives an emotion code assigned to the button object B530a.

After step S530, the cosmetic dispenser 50 executes a recipe request (S531).

Specifically, the processor 52 transmits recipe request data to the server 30.

The recipe request data includes the following information:
machine ID of the cosmetic dispenser 50; and
emotion code received in step S530

After step S531, the server 30 executes selecting recipe (S330).

Specifically, the processor 32 refers to the machine information database (FIG. 11) and specifies the owner user ID associated with the machine ID included in the recipe request data.

The processor 32 refers to the skin evaluation log information database (FIG. 10) associated with the specified owner user ID, and specifies the latest skin score (for example, the first skin score of the record including the information indicating the first date of the latest date and time stored in the "date and time" field).

The processor 32 refers to the recipe information database (FIG. 12) and specifies a record in which the specified skin score is included in the information in the "condition" field.

The processor 32 specifies a record in which the emotion code included in the recipe request data matches the information stored in the "emotion condition" field among the specified records.

The processor 32 specifies the recipe ID and the usage amount of each cosmetic in the specified record (that is, the record based on the skin score and the emotion code).

After step S330, steps S321, S522 to S524, and S322 are executed in the same manner as in FIG. 16.

According to the first variation, a recipe based on the user's emotion is selected.

As a result, it is possible to provide a cosmetic that is more suitable for user-unique factors.

(5-2) Second Variation

A second variation will be described.

The second variation is an example of information processing when the cartridges CA1 to CA5 are replaced.

Figure 21:
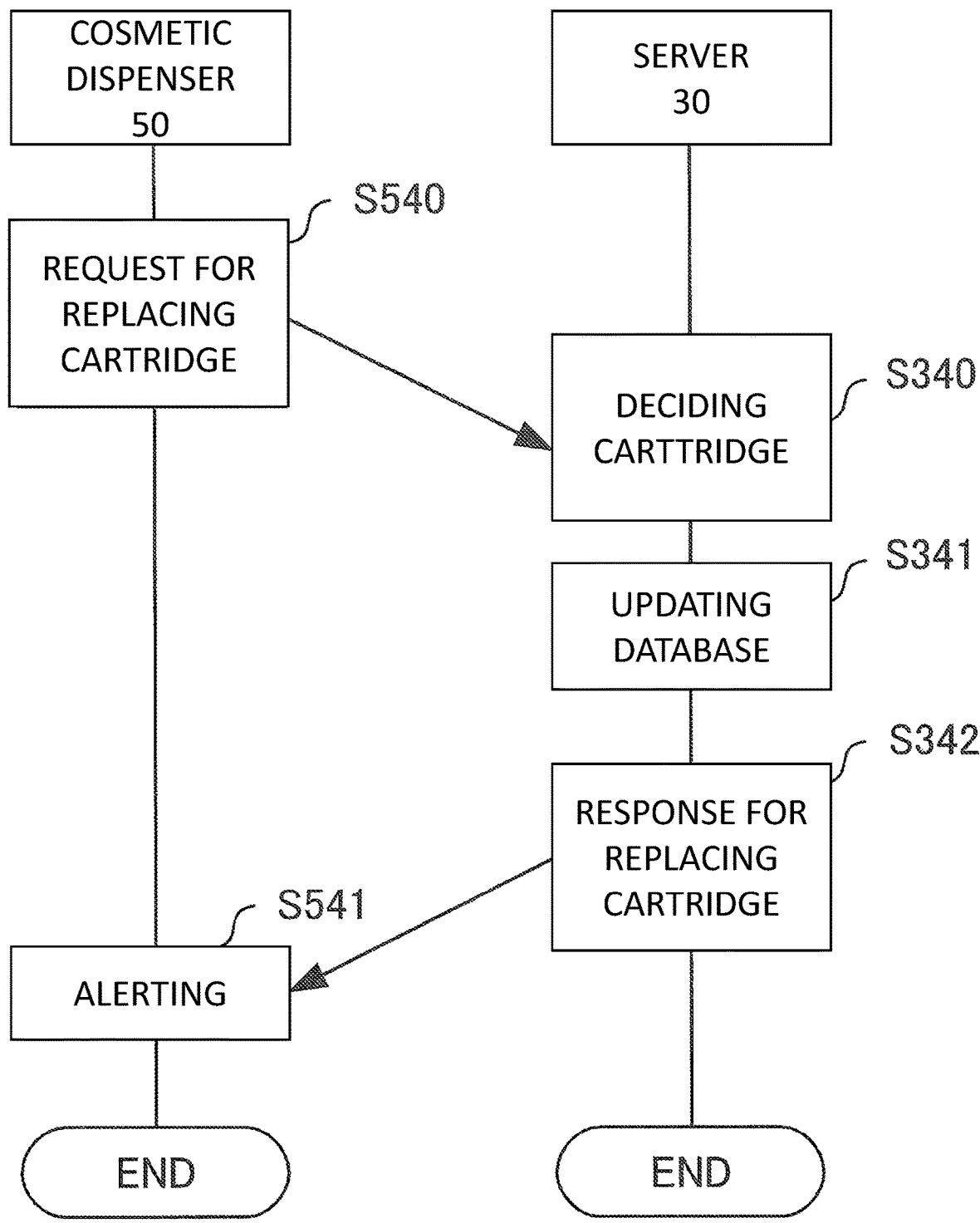
FIG. 21 is a flowchart of cartridge replacement processing according to a second variation.

FIG. 21 is a flowchart of the cartridge replacement process of the second variation.

As shown in FIG. 21, the cosmetic dispenser 50 executes a cartridge replacement request (S540).

Specifically, after the user opens the upper part 50a and replaces the cartridge CA in the cartridge slots 50aa to 50ae and then closes the upper part 50a, the processor 52 transmits cartridge replacement request data to the server 30.

The cartridge replacement request data includes the following information:
machine ID of cosmetic dispenser 50;
cartridge ID stored in IC chip CAa of the newly attached cartridge CA;
remaining value stored in IC chip CAa of the newly attached cartridge CA; and
information indicating the type of cosmetic stored in the IC chip CAa of the newly attached cartridge CA.

In the case that the newly attached cartridge CA is a non-genuine product, the cartridge replacement request data may not include at least one of the cartridge ID, the remaining value, and the type of cosmetic.

After step S540, the server 30 executes determining cartridge (S340).

Specifically, when the cartridge ID included in the cartridge replacement request data is not the predetermined cartridge ID, or when the cartridge replacement request data does not include the cartridge ID, the processor 32 determines that the newly attached cartridge CA is a non-genuine product.

After step S340, the server 30 executes updating database (S341).

Specifically, the processor 32 refers to the machine information database (FIG. 11) and specifies a record including the machine ID included in the cartridge replacement request data.

The processor 32 stores the cartridge ID and the remaining amount value included in the cartridge replacement request data in the "cartridge" field of the specified record.

In the case that the processor 32 determines in step S340 that the product is a non-genuine product, the processor 32 may store a code indicating the non-genuine product in the "cartridge" field.

After step S341, the server 30 executes a cartridge replacement response (S342).

Specifically, the processor 32 transmits cartridge replacement response data to the cosmetic dispenser 50.

If it is determined as non-genuine product in step S340, the cartridge replacement response data includes a message indicating that the newly attached cartridge CA is a non-genuine product.

After step S342, the cosmetic dispenser 50 executing alerting (S541).

Specifically, the processor 52 displays a message included in the cartridge replacement response data on the display.

According to the second variation, the server 30 may store the information indicating that the newly attached cartridge CA is a non-genuine product and alert this information to the user.

(5-3) Third Variation

A third variation will be described.

The third variation is an example of the configuration of the cosmetic dispenser 50.

(5-3-1) Configuration of Cosmetic Dispenser

The configuration of the cosmetic dispenser of the third variation will be described.

Figure 22:
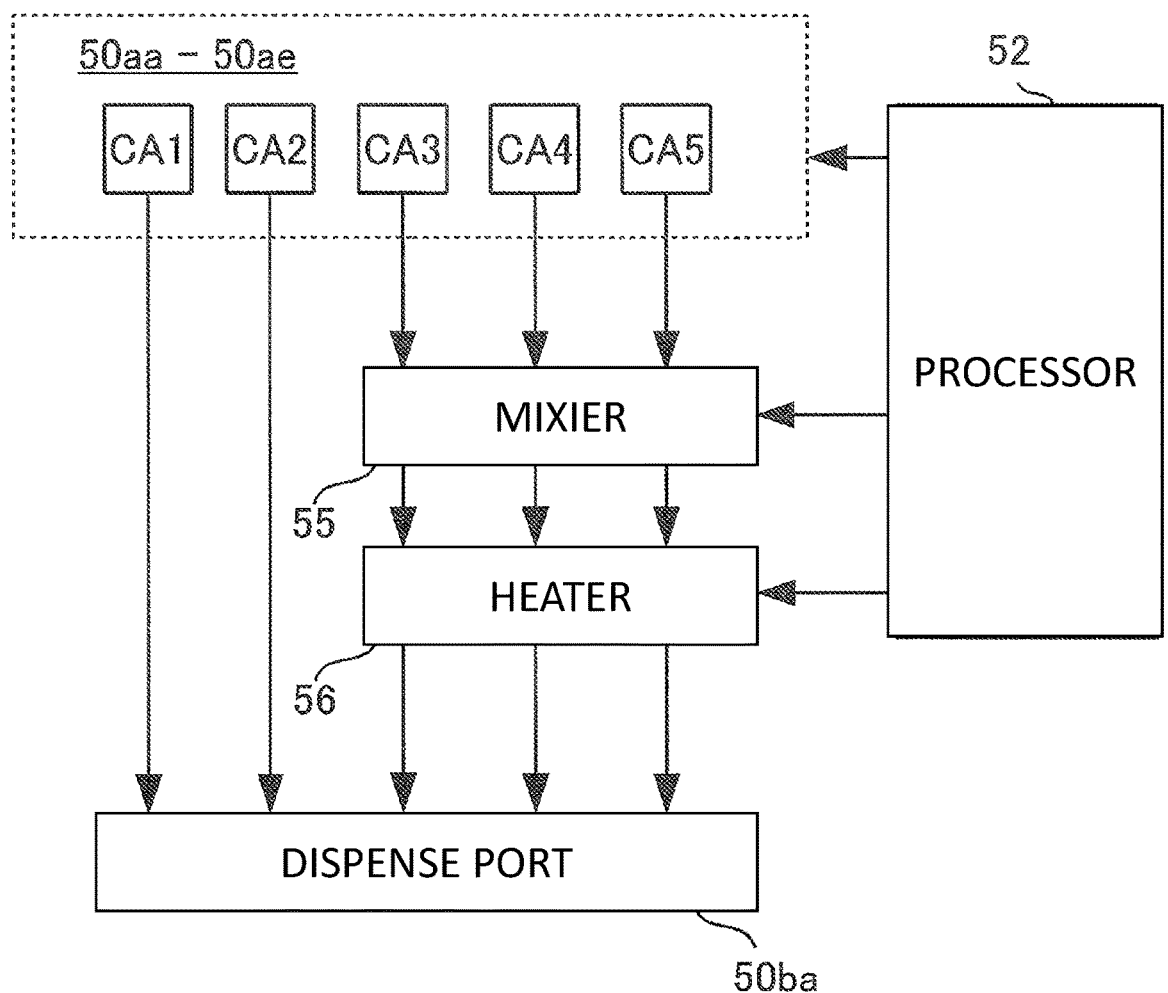
FIG. 22 is a schematic diagram showing a configuration of a cosmetic dispenser according to a third variation.

FIG. 22 is a schematic diagram illustrating a configuration of a cosmetic dispenser according to a third variation.

As shown in FIG. 22, the cosmetic dispenser 50 includes a mixer 55 and a heater 56 in addition to the configuration of FIG. 3.

The mixer 55 is configured to mix cosmetics contained in the cartridges CA3 to CA5.

The processor 52 controls the mixer 55 to mix and dispense the cosmetics contained in the cartridges CA3 to CA5.

The cosmetics to be mixed are not limited to the cosmetics contained in the cartridges CA3 to CA5.

Cosmetics contained in the cartridges CA1 to CA5 may be mixed.

The heater 56 is configured to heat the cosmetics contained in the cartridges CA3 to CA5.

The processor 52 controls the heater 56 to heat and dispense the cosmetics contained in the cartridges CA3 to CA5.

The cosmetics to be heated are not limited to the cosmetics contained in the cartridges CA3 to CA5.

Cosmetics contained in the cartridges CA1 to CA5 may be heated.

(5-3-2) Recipe Information Database

A recipe information database of the third variation will be described.

FIG. 23 is a diagram illustrating a data structure of a recipe information database according to the third variation.

As shown in FIG. 23, the recipe information database of the third variation includes a "mixer" field and a "heater" field in addition to the fields shown in FIG. 12.

The "mixer" field includes a "mixing speed" field, a "mixing order" field, and a "mixing time" field.

The "mixing speed" field stores a value indicating the mixing speed by the mixer 55.

The "mixing order" field stores cartridge slot IDs indicating the mixing order by the mixer 55.

The cartridge slot ID is information for identifying the cartridge slots 50ac to 50ae.

The "mixing time" field stores a value indicating the mixing time by the mixer 55.

The "heater" field includes a "heating temperature" field and a "heating time" field.

The "heating temperature" field stores a value indicating the heating temperature of the heater 56.

The "heating time" field stores a value indicating the heating time of the heater 56.

(5-3-3) Dispensing Cosmetics

A process of dispensing cosmetics according to the third variation will be described.

In step S320 of FIG. 16, the processor 32 specifies a record whose skin score is included in the range indicated by the information in the "condition" field, and then specifies the recipe ID, the usage amount of each cosmetic, and the control information (heating temperature and heating time), of the specified.

In step S321, the processor 32 transmits recipe response data to the cosmetic dispenser 50.

The recipe response data includes the following information:

recipe ID specified in step S320;

usage amount of each cosmetic specified in step S320;

control information of the mixer 55 specified in step S320; and control information of the heater 56 specified in step S320.

In step S523, the processor 52 controls the cartridges CA3 to CA5, the mixer 55, and the heater 56 based on the usage amount and the control information included in the recipe response data.

According to the third variation, the user may receive the cosmetics mixed and heated based on the user unique information.

(5-4) Fourth Variation

A fourth variation will be described.

The fourth variation is an example in which the emulsion and cosmetic liquid are contained in the cartridge CA.

The different types of emulsions may be contained in the cartridges CA1 to CA2 of the fourth variation, and different types of cosmetic liquids may be contained in the cartridges CA3 to CA5.

For example, the emulsion contained in the cartridge CA1 is dispensed when the process of dispensing cosmetics is executed in the time zone after waking up (for example, 6:00 to 8:00).

That is, the emulsions contained in the cartridge CA1 is a emulsion for morning use.

The emulsion for morning use contain ingredients suitable for utilization prior to a day's activity.

The emulsion contained in the cartridge CA2 is dispensed when the process of dispensing cosmetics is executed in a time zone before going to bed (for example, 22:00 to 24:00).

That is, the emulsion contained in the cartridge CA1 is an emulsion for night use.

The emulsion for night use contains ingredients suitable for utilization before going to bed.

The cosmetic liquid contained in the cartridges CA3 to CA5 is dispensed based on the recipe information.

(5-5) Fifth Variation

A fifth variation will be described.

The fifth variation is an example in which the preparation used for the makeup is contained in the cartridge CA.

As a first example, the cartridge CA1 contains a preparation that gives a weakly glossy texture (so-called matte texture).

The cartridge CA2 contains a preparation that gives a glossy texture.

The cartridge CA3 contains a moisturizer.

The moisturizer is, for example, a preparation that moisturizes the skin, a preparation that prevents ultraviolet rays, or a combination thereof.

The cartridge CA4 contains a foundation having a color tone (hue and saturation in the Munsell color system) that matches the user's skin color and high brightness.

The cartridge CA5 contains a foundation having a color tone (hue and saturation in the Munsell color system) that matches the user's skin color and low brightness.

In step S320, the processor 32 specifies the owner user ID, refers to the skin log information database (FIG. 9) associated with the specified owner user ID, and specifies the latest skin color (for example, the skin color of the record in which the information of "data and time" field is the latest).

In the case that the specified skin color is lighter than a predetermined threshold, the processor 32 selects a recipe having a high blending ratio of the formulation contained in the cartridge CA4.

In the case that the specified skin color is darker than a predetermined threshold value, the processor 32 selects a recipe having a high blending ratio of the formulation contained in the cartridge CA5.

The second example differs from the first example in the following points:
the cartridge CA4 contains a foundation that has a color tone
   that matches the user's skin color (hues, saturation, and brightness in the Munsell color system) and that has a high cover level; and
the cartridge CA5 contains a foundation that has a tone that
   matches the user's skin color (hues, saturation, and brightness in the Munsell color system) and that has a low cover level.

The cover level is the magnitude of the effect of hiding skin spots and freckles.

In step S320, after specifying the owner user ID, the processor 32 refers to the skin log information database (FIG. 9) associated with the specified owner user ID and specifies the latest moisture content (for example, the moisture content of the record whose the information of the "date and time" field indicates the latest date and time).

When the specified amount of water is higher than a predetermined threshold, the processor 32 selects a recipe having a high blending ratio of the formulation contained in the cartridge CA4.

Alternatively, the processor 32 selects a recipe having a low blending ratio of the moisturizer contained in the cartridge CA3.

When the specified amount of water is equal to or less than the predetermined threshold, the processor 32 selects a recipe having a high blending ratio of the formulation contained in the cartridge CA5.

Alternatively, the processor 32 selects a recipe having a high blending ratio of the moisturizer contained in the cartridge CA3.

(5-6) Sixth Variation

A sixth variation will be described.

The sixth variation is an example in which a predetermined notification is given to the user when the remaining amount of cosmetics contained in the cartridge CA has been little.

Figure 24:
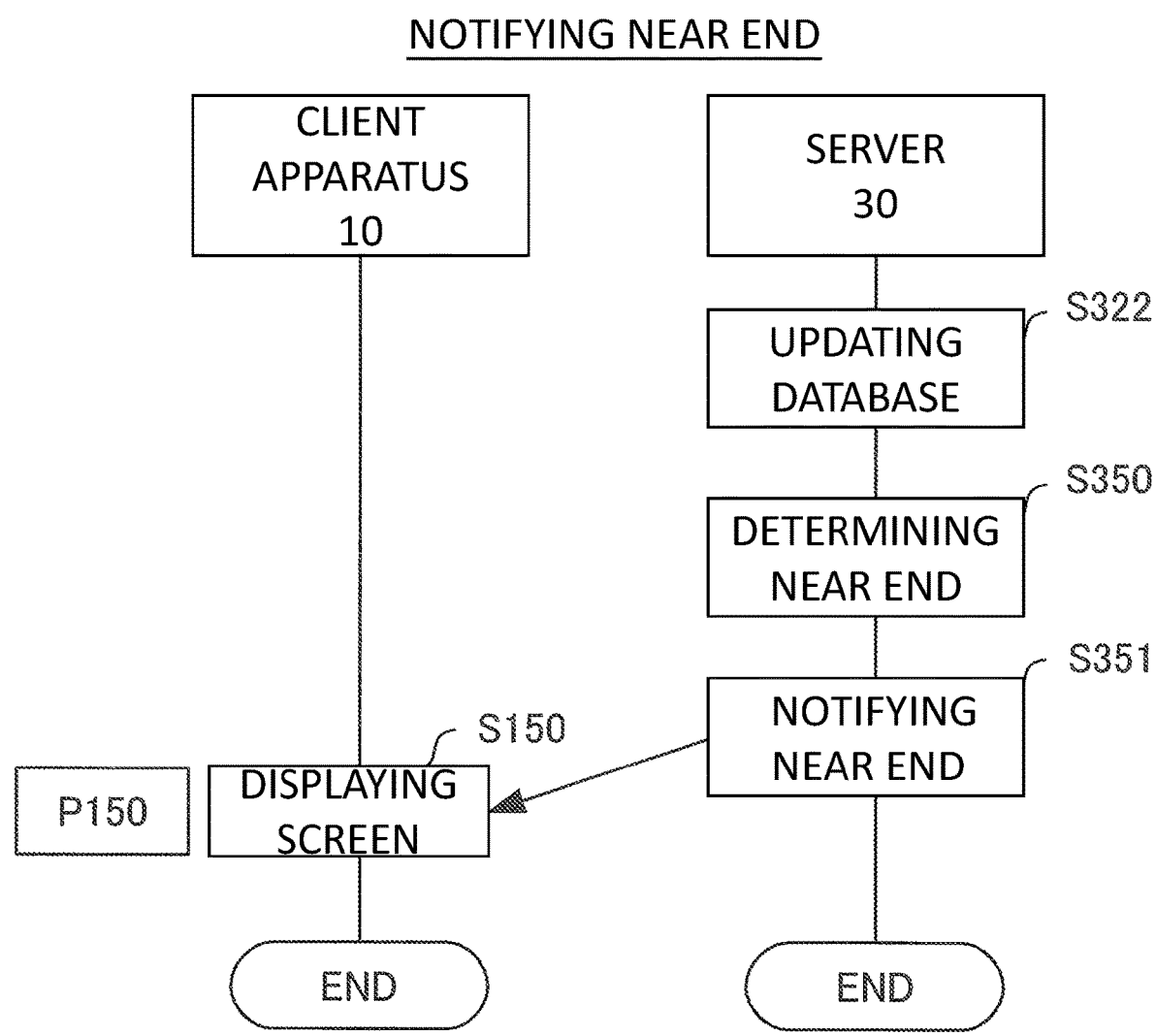
FIG. 24 is a flowchart of a near-end notification process according to a sixth variation.

FIG. 24 is a flowchart of the near-end notification process according to the sixth variation.

Figure 25:
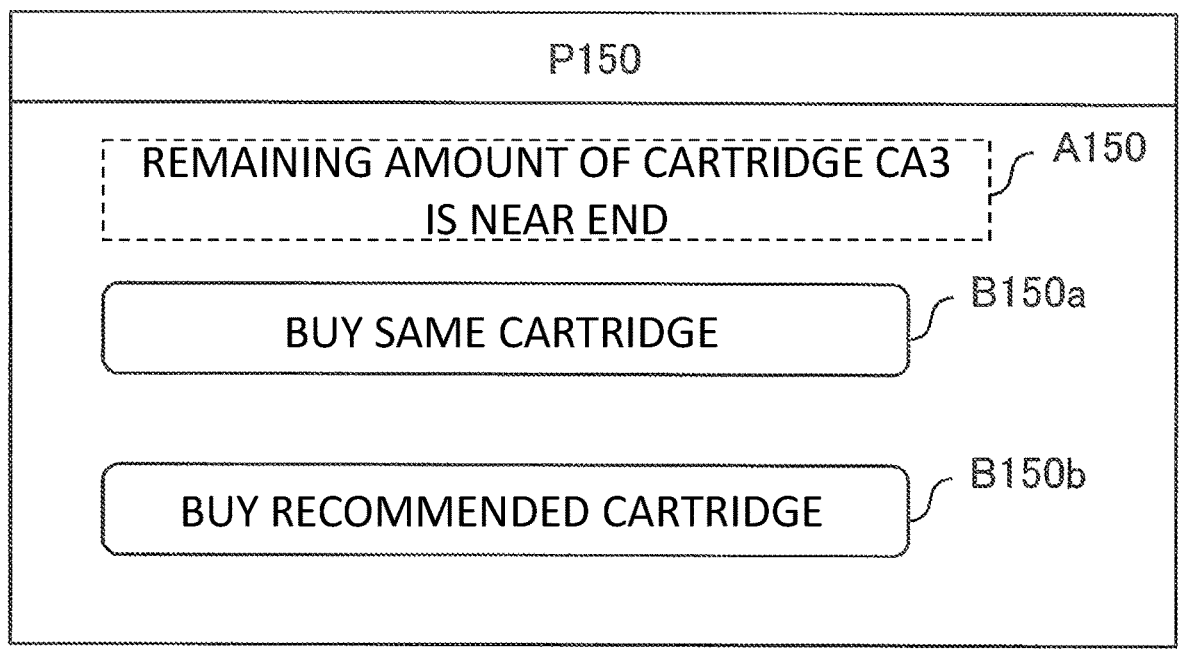
FIG. 25 is a diagram showing an example of a screen displayed in the information process of FIG. 24.

FIG. 25 is a diagram of a screen example displayed in the information processing of FIG. 24.

As shown in FIG. 24, the server 30 executes determining near-end (S350) after step S322 (FIG. 16).

Specifically, the processor 32 refers to the machine information database (FIG. 11) updated in step S322, and specifies the cartridge (hereinafter referred to as "near-end cartridge") whose the remaining amount value of the "cartridge" field is equal to or less than a predetermined threshold.

The server 30 executes notifying near-end (S351).

Specifically, the processor 32 transmits near-end notification data to the client apparatus 10 in which the cosmetic dispense application associated with the owner user ID specified in step S320 is installed.

The client apparatus 10 executes displaying screen (S150) based on the near-end notification data.

Specifically, the processor 12 displays the screen P150 on the display.

The screen P150 includes display object A150 and button objects B150a to B150b.

The display object A150 indicates a message indicating the cartridge specified as the near-end cartridge in step S350.

A URL (Uniform Resource Locator) of a purchase site for purchasing a cartridge of the same type as the cartridge specified as the near-end cartridge is assigned to the button object B150a.

When the user operates the button object B150a, the processor 12 accesses the URL assigned to the button object B150a.

A URL of a purchase site for purchasing a cartridge recommended for the user is assigned to the button object B150b.

When the user operates the button object B150b, the processor 12 accesses the URL assigned to the button object B150b.

In the sixth variation, the server 30 may execute the purchase and delivery processing for the cartridge specified as the near-end cartridge, instead of the notifying near-end (S351).

In this case, the user may receive a new cartridge without any operation.

According to the sixth variation, the user may utilization the cosmetic dispenser 50 without paying mind to the remaining amount of the cartridge.

(5-7) Seventh Variation

The seventh variation will be described.

The seventh variation is an example in which a recipe is selected based on information stored in the prediction information providing server 70.

FIG. 26 is a flowchart of a process for dispensing cosmetics according to the seventh variation.

As shown in FIG. 26, after step S521 (FIG. 16), the server 30 executes a prediction information request (S360).

Specifically, the processor 32 refers to the machine information database (FIG. 11) and specifies the owner user ID associated with the machine ID included in the recipe request data.

The prediction information providing server 70 stores a user ID, environment prediction information, action prediction information, and psychosomatic prediction information in association with each other.

The processor 32 transmits the prediction information request data to the prediction information providing server 70.

The prediction information request data includes the specified owner user ID.

After step S360, the prediction information providing server 70 executes specifying prediction information (S760).

Specifically, the prediction information providing server 70 specifies prediction information (at least one of environmental prediction information, action prediction information, and psychosomatic prediction information) associated with the user ID included in the prediction information request data.

After step S760, the prediction information providing server 70 executes a prediction information response (S761).

Specifically, the prediction information providing server 70 transmits prediction information response data to the server 30.

The prediction information response data includes the prediction information specified in step S760.

After step S761, the server 30 executes selecting recipe (S361).

As a first example, the processor 32 specifies the latest skin score and then corrects the skin score based on the prediction information included in the prediction information response data.

As an example, when the prediction information is environment prediction information indicating a rain forecast, the processor 32 corrects the skin score assuming that the user goes to an environment with high humidity.

As another example, when the prediction information is action prediction information indicating exercise, the processor 32 corrects the skin score assuming that the user exercises.

As another example, when the prediction information is psychosomatic prediction information related to the psychosomatic, the processor 32 corrects the skin score assuming that the amount of sebum secretion increases (that is, deterioration of the skin condition).

The processor 32 refers to the recipe information database (FIG. 12) and specifies a record in which the corrected skin score is included in the range indicated by the information in the "condition" field.

The processor 32 specifies the recipe ID and the usage amount of each cosmetic of the specified record.

As a second example, the same preparation as that of the first example of the fifth variation is contained in the cartridges CA1 to CA5.

The "condition" field of the recipe information database (FIG. 12) stores the contents of the prediction information as a reference when selecting recipe information.

The content of the prediction information indicates an event that does not affect the skin condition.

The processor 32 refers to the recipe information database (FIG. 12) and specifies a record whose information in the "condition" field matches the prediction information.

The processor 32 specifies the recipe ID of the specified record and the usage amount of each cosmetic.

As an example, when the action prediction information indicates an action in which a glossy make is preferred (for example, participation in a party), the processor 32 selects the recipe indicating the blending ratio of the formulation contained in the cartridge CA2 higher than that in the cartridge CA1.

As another example, when the action prediction information indicates an action (participation in a business meeting) in which conservative make is preferred, the processor 32 selects the recipe indicating the mixing ratio of the formulation contained in the cartridge CA1 higher than that in the cartridge CA2.

According to the seventh variation, the user may be provided with a customized cosmetic product suitable to both the user log information (that is, factors unique to the past user) and the prediction information (that is, factors specific to the future user).

(5-8) Eighth Variation

The eighth variation will be described.

The eighth variation is an example in which a recipe is selected in consideration of prediction information.

In step S320 (FIG. 16), after specifying the owner user ID, the processor 32 specifies either the first skin score or the second skin score according to the execution time of the process.

For example, when the execution time is from 6:00 to 8:00, the processor 32 specifies the latest first skin score.

When the execution time is 22:00 to 24:00, the processor 32 specifies the latest second skin score.

The processor 32 refers to the recipe information database (FIG. 12) and specifies a record in which the specified skin score (first skin score or second skin score) is included in the range indicated by the information in the "condition" field.

The processor 32 specifies the recipe ID and the usage amount of each cosmetic of the specified record.

According to the eighth variation, the skin score to be referenced for selecting a recipe is switched according to the time when the user uses the cosmetic dispenser 50.

In particularly, after waking up, a recipe is selected with reference to the first skin score based on past user-unique information.

Before going to bed, a recipe is selected with reference to the second skin score based on past user unique information and future user unique information.

Thereby, the customized cosmetics suitable for a user's lifestyle may be provided.

(5-9) Ninth Variation

The ninth variation will be described.

The ninth variation is an example in which the amount of cosmetics dispensed by the cosmetic dispenser 50 is adjusted for each user.

The user information database (FIG. 5) further stores size information indicating the size of a part (for example, a face) to which cosmetics are to be applied.

The size information may be determined based on a user instruction or may be estimated from the image of the part.

In step S321 (FIG. 16), the server 30 specifies size information associated with the owner user ID specified in step S320.

The server 30 transmits recipe response data to the cosmetic dispenser 50.

The recipe response data includes the following information:
the recipe ID specified in step S320;
the usage amount specified step S320; and
the specified size information.

In step S523, the cosmetic dispenser 50 determines the usage amount of the cosmetic to be dispensed on the basis of the size information included in the recipe response data.

Specifically, the processor 52 determines the usage amount of the cosmetic based on the size information.

The processor 52 controls the cartridges CA1 to CA5 so that the cosmetics contained in the cartridges CA1 to CA5 are dispensed by the determined usage amount.

The usage amount of cosmetics may be the dispense amount of each of the cartridges CA1 to CA5, or the total amount of cosmetics dispensed from the cartridges CA1 to CA5.

According to the eighth variation, it may provide an amount of customized cosmetics suitable for the user.

(6) Summary of Present Embodiment

The present embodiment will be summarized.

The first aspect of the present embodiment is an information processing apparatus (for example, a server 30) capable of communicating with a cosmetic dispenser 50 configured to dispense at least one of a plurality of cosmetics based on recipe information (FIG. 12) indicating a usage amount of each of the plurality of cosmetics, the apparatus comprising:

a retrieve module (for example, the processor 32 executing step S320) configured to retrieve user-unique information unique to the user, the user-unique information including at least one of user attribute information related to the user's attributes, environmental information related to the user's environment, action information related to the user's action, and psychosomatic information related to the user's psychosomatic, skin information related to the user's skin, and information related to cosmetics which the user has used;

a selection module (for example, the processor 32 executing step S320) configured to select the recipe information based on the user unique information among a plurality of recipe information; and a transmission module (for example, the processor 32 executing step S321) configured to transmit the selected recipe information to the cosmetic dispenser.

According to the first aspect, it is possible to provide a customized cosmetic suitable for a user-specific factor.

In particularly, it is possible to provide a customized cosmetic suitable for at least one of the user's attributes, the user's environment, the user's action, the user's psychosomatic, the user's skin, and cosmetics which the user has used.

In the second aspect of the present embodiment, the user attribute information includes information indicating at least one of age, gendar, and address of the user.

In the third aspect of the present embodiment, the environmental information includes information indicating at least one of the temperature, humidity, and UV exposure amount of the environment spent by the user.

In the fourth aspect of the present embodiment, the action information includes information indicating at least one of meal, exercise, sleep, energy consumption, and location of the user.

In the fifth aspect of the present embodiment, the psychosomatic information includes a pulse value, a sexual cycle, stress index, and mindfulness index, height, weight, body fat, a skin humidity retention level, a skin wrinkle level, and a skin spot level of the user.

In the sixth aspect of the present embodiment, the recipe information includes information indicating a usage amount or a blending ratio of the cosmetics contained in each cartridge.

In the seventh aspect of the present embodiment, the user unique information includes user log information (FIGS. 6 to 10) indicating the history of the user unique information.

In the eighth aspect of the present embodiment, further comprising a module (for example, the processor 32 executing step S341) configured to store cartridge information related to a cartridge CA containing the cosmetics associated with machine ID that identifies the cosmetic dispenser 50.

According to the eighth aspect, the server 30 may manage information (FIG. 11) on the cartridge CA set in the cosmetic dispenser 50.

In the ninth aspect of the present embodiment, the cartridge information includes information (FIG. 11) indicating a remaining amount of cosmetics contained in the cartridge.

According to the ninth aspect, the server 30 may manage the remaining amount of cosmetics contained in the cartridge CA set in the cosmetic dispenser 50.

A tenth aspect of the present embodiment is a cosmetic dispenser 50 capable of communicating with the information processing apparatus (for example, server 30), the cosmetic dispenser 50 comprising:

a plurality of cartridge slots 50*aa* to 50*ae* configured to hold cartridges CA containing cosmetics, each cartridge detachable with each cartridge slot; and a dispenser (for example, the processor 52 executing step S522) configured to use the cosmetic contained in each cartridge CA held by each cartridge slot 50*aa* to 50*ae* based on the recipe information transmitted from the information processing apparatus (for example, server 30) and dispense the cosmetic corresponding to the recipe information.

In the eleventh aspect of the present embodiment, the dispenser dispenses the cosmetics contained in each cartridge CA based on the recipe information.

In the twelfth aspect of the present embodiment, the dispenser mixes the cosmetics contained in the cartridges and dispenses the mixed cosmetics based on the recipe information.

In the thirteenth aspect of the present embodiment, further comprising a transmission module (for example, the processor 52 executing step S523) configured to transmit cartridge information relating to the cartridge CA held in the cartridge slots 50*aa* to 50*ae* to the information processing apparatus (for example, the server 30).

In the fourteenth aspect of the present embodiment, the cartridge information includes information indicating the remaining amount of cosmetics contained in the cartridge CA.

(7) Other Variations

The memory 11 may be connected to the client apparatus 10 via the network NW.

The memory 31 may be connected to the server 30 via the network NW.

The memory 51 may be connected to the cosmetic dispenser 50 via the network NW.

Each step of the above information processing may be executed by any one of the client apparatus 10, the server 30, and the cosmetic dispenser 50.

The recipe information database (FIG. 12) may include a "blending ratio" field instead of the "usage amount" field.

The "blending ratio" field stores information indicating the blending ratio of the cosmetics contained in the cartridges CA1 to CA5.

In step S523 (FIG. 16), the processor 52 dispenses the cosmetics contained in the cartridges CA1 to CA5 so that the total amount of the cosmetics to be dispensed becomes a constant amount at a rate based on the information indicating the blending ratio.

This example is particularly preferable when the preparation used for the makeup is contained in the cartridge CA as in the fifth variation.

The server 30 may retrieve the user log information (at least one of environment log information, action log information, and psychosomatic log information) from an apparatus (for example, an external server) other than the wearable device 90.

In this case, the external server stores a user ID and user log information in association with each other.

The psychosomatic log information may further include the following information:
user's height;
user's weight; and
user's body fat.

The skin log information may further include the following information:
information indicating the skin humidity retention level;
information indicating the level of skin wrinkles; and
information indicating the level of skin spots.

The server 30 may further select a recipe based on at least one of the following:
user attribute information (FIG. 5);
used cosmetic ID (FIG. 5); and
interview (FIG. 5).

The skin log information database of FIG. 9 includes a "skin color" field, a "water content" field, and "sebum" field which store the measurement value measured by the measurement apparatus.

Although the embodiments of the present invention have been described in detail above, the scope of the present invention is not limited to the above-described embodiments.

Further, various modifications and changes may be applied to the above embodiments without departing from the subject matter of the present invention.

In addition, the above embodiments and variations may be combined.

REFERENCE SIGNS LIST

1: Information processing system
10: Client apparatus
11: Memory
12: Processor
13: I/O interface
14: Communication interface
15: GPS module
16: Camera
30: Server
31: Memory
32: Processor
34: Communication interface
50: Cosmetic dispenser
51: Memory
52: Processor
53: I/O interface
54: Communication interface
55: Mixer
56: Heater
70: Predictive information providing server
90: Wearable device

The invention claimed is:

1. An information processing apparatus capable of communicating with a cosmetic dispenser configured to dispense at least one of a plurality of cosmetics based on recipe information indicating a usage amount of each of the plurality of cosmetics, the apparatus comprising:
   a retrieve module configured to retrieve user-unique information unique to the user and prediction information, the user-unique information including at least one of user attribute information related to the user's attributes, environmental information related to the user's environment, action information related to the user's action, psychosomatic information related to the user's psychosomatic, skin information related to the user's skin, and information related to cosmetics which the user has used;
   a selection module configured to select the recipe information based on the user-unique information and the prediction information among a plurality of recipe information, the user-unique information including user log information indicating a history of the user-unique information;
   a calculator configured to calculate a first skin score based on the user log information and a second skin score based on the prediction information; and
   a transmission module configured to transmit the selected recipe information to the cosmetic dispenser,
   wherein the selection module selects the recipe information based on the first skin score and the second skin score.

2. The information processing apparatus according to claim 1, wherein the user attribute information includes information indicating at least one of age, gender, and address of the user.

3. The information processing apparatus according to claim 1, wherein the environmental information includes information indicating at least one of a temperature, a humidity, and an ultraviolet exposure amount of the environment spent by the user.

4. The information processing apparatus according to claim 1, wherein the action information includes information indicating at least one of meal, exercise, sleep, energy consumption, and location of the user.

5. The information processing apparatus according to claim 1, wherein the psychosomatic information includes a pulse value, a sexual cycle, stress index, mindfulness index, height, weight, body fat, a skin humidity retention level, a skin wrinkle level, and a skin spot level of the user.

6. The information processing apparatus according to claim 1, wherein the recipe information includes information indicating a usage amount of cosmetics or information indicating a blending ratio of cosmetics.

7. The information processing apparatus according to claim 1, further comprising a module configured to store cartridge information relating to a cartridge containing the cosmetic associated with machine ID that identifies the cosmetic dispenser.

8. The information processing apparatus according to claim 7, wherein the cartridge information includes information indicating a remaining amount of cosmetics contained in the cartridge.

9. A cosmetic dispenser capable of communicating with the information processing apparatus according to claim 1, the cosmetic dispenser comprising:
   a plurality of cartridge slots configured to hold cartridges containing cosmetics, each cartridge detachable with each cartridge slot; and
   a dispenser configured to use the cosmetic contained in each cartridge held by each cartridge slot based on the recipe information transmitted from the information processing apparatus and dispense the cosmetic corresponding to the recipe information.

10. The cosmetic dispenser according to claim 9, wherein the dispenser dispenses the cosmetic contained in each cartridge based on the recipe information.

11. The cosmetic dispenser according to claim 9, wherein the dispenser mixes the cosmetics contained in the cartridges and dispenses the mixed cosmetics based on the recipe information.

12. The cosmetic dispenser according to claim 9, further comprising a transmission module configured to transmit cartridge information relating to the cartridge held in the cartridge slot to the information processing apparatus.

13. The cosmetic dispenser according to claim 12, wherein the cartridge information includes information indicating a remaining amount of the cosmetic contained in the cartridge.

14. The information processing apparatus according to claim 1, wherein the prediction information includes at least one of environment prediction information indicating prediction of future environment, action prediction information indicating prediction of future user action, or psychosomatic prediction information indicating prediction of the user's psychosomatic.

15. A computer-implemented method for providing recipe information indicating a usage amount of each of the plurality of cosmetics to a cosmetic dispenser configured to dispense at least one of a plurality of cosmetics based on the recipe information, the method comprising:
    retrieving user-unique information unique to the user and prediction information, the user-unique information including at least one of user attribute information related to the user's attributes, environmental information related to the user's environment, action information related to the user's action, psychosomatic information related to the user's psychosomatic, skin information related to the user's skin, and information related to cosmetics which the user has used;
    selecting the recipe information based on the user-unique information and the prediction information among a plurality of recipe information, the user-unique information including user log information indicating a history of the user-unique information;
    calculating a first skin score based on the user log information and a second skin score based on the prediction information; and
    transmitting the selected recipe information to the cosmetic dispenser,
    wherein the selecting comprises selecting the recipe information based on the first skin score and the second skin score.

16. The method to claim 15, wherein the psychosomatic information includes a pulse value, a sexual cycle, stress index, mindfulness index, height, weight, body fat, a skin humidity retention level, a skin wrinkle level, and a skin spot level of the user.

17. The method according to claim 15, wherein the recipe information includes information indicating a usage amount of cosmetics or information indicating a blending ratio of cosmetics.

18. The method according to claim 15, wherein the prediction information includes at least one of environment prediction information indicating prediction of future environment, action prediction information indicating prediction of future user action, or psychosomatic prediction information indicating prediction of the user's psychosomatic.

* * * * *